US012171412B2

(12) United States Patent
Giegerich et al.

(10) Patent No.: US 12,171,412 B2
(45) Date of Patent: Dec. 24, 2024

(54) DENTAL IMAGING SYSTEM AND METHOD

(71) Applicant: Alta Smiles LLC, Fort Washington, PA (US)

(72) Inventors: Gary D. Giegerich, Fort Washington, PA (US); Talia Shemesh, Fort Washington, PA (US)

(73) Assignee: ALTA SMILES LLC, Fort Washington, PA (US)

( * ) Notice: Subject to any disclaimer, the term of this patent is extended or adjusted under 35 U.S.C. 154(b) by 0 days.

(21) Appl. No.: 18/688,171

(22) PCT Filed: Sep. 7, 2022

(86) PCT No.: PCT/US2022/042734
§ 371 (c)(1),
(2) Date: Feb. 29, 2024

(87) PCT Pub. No.: WO2023/038954
PCT Pub. Date: Mar. 16, 2023

(65) Prior Publication Data
US 2024/0366080 A1    Nov. 7, 2024

Related U.S. Application Data

(60) Provisional application No. 63/286,299, filed on Dec. 6, 2021, provisional application No. 63/241,367, filed on Sep. 7, 2021.

(51) Int. Cl.
*A61B 1/247*    (2006.01)
*A61B 1/06*    (2006.01)
(Continued)

(52) U.S. Cl.
CPC ............... *A61B 1/247* (2013.01); *A61B 1/06* (2013.01); *A61B 1/32* (2013.01); *A61C 7/002* (2013.01); *A61C 9/0053* (2013.01)

(58) Field of Classification Search
None
See application file for complete search history.

(56) References Cited

U.S. PATENT DOCUMENTS

| 1,042,133 A | 10/1912 | Marshall |
|---|---|---|
| D634,841 S | 3/2011 | Tao |

(Continued)

FOREIGN PATENT DOCUMENTS

| WO | 2006105476 A2 | 10/2006 |
|---|---|---|
| WO | 2011066510 A2 | 6/2011 |
| WO | 2020232223 A1 | 11/2020 |

OTHER PUBLICATIONS

International Search Report and Written Opinion in International Application No. PCT/US2022/42734 dated Feb. 14, 2023.
(Continued)

*Primary Examiner* — Rebecca A Volentine
(74) *Attorney, Agent, or Firm* — Panitch Schwarze Belisario & Nadel LLP

(57) ABSTRACT

A dental imaging system for capturing images of a patient's arches and teeth includes a central processor for storing images, a camera having a camera lens and a camera housing, and a camera holder having a tray, an angled column extending from a front of the tray and an engagement mechanism positioned at a distal end of the angled column. The engagement mechanism is configured to releasably engage the camera to orient the camera lens toward the patient's arches and teeth.

20 Claims, 19 Drawing Sheets

(51) Int. Cl.
  *A61B 1/32*    (2006.01)
  *A61C 7/00*    (2006.01)
  *A61C 9/00*    (2006.01)

(56) References Cited

U.S. PATENT DOCUMENTS

| | | |
|---|---|---|
| 10,076,389 B2 | 9/2018 | Wu et al. |
| 2006/0078842 A1 | 4/2006 | Sachdeva et al. |
| 2006/0199137 A1 | 9/2006 | Abels et al. |
| 2006/0252003 A1 | 11/2006 | Taub et al. |
| 2009/0076321 A1 | 3/2009 | Suyama et al. |
| 2009/0191503 A1 | 7/2009 | Matov et al. |
| 2009/0230161 A1 | 9/2009 | Emsky |
| 2014/0050298 A1 | 2/2014 | Lee |
| 2014/0122027 A1 | 5/2014 | Andreiko et al. |
| 2015/0132707 A1 | 5/2015 | Huang et al. |
| 2016/0270881 A1 | 9/2016 | Taub et al. |
| 2018/0064326 A1 | 3/2018 | Patrick et al. |
| 2018/0204332 A1 | 7/2018 | Salah et al. |
| 2018/0228359 A1* | 8/2018 | Meyer ..................... A61B 1/24 |
| 2018/0303331 A1 | 10/2018 | Salah et al. |
| 2018/0303583 A1 | 10/2018 | Tong et al. |
| 2019/0252068 A1 | 8/2019 | Katzman et al. |
| 2020/0146794 A1 | 5/2020 | Lee et al. |
| 2020/0289241 A1 | 9/2020 | Kronenberg |
| 2020/0297205 A1* | 9/2020 | Hill ......................... A61B 1/24 |
| 2021/0068923 A1 | 3/2021 | Carrier, Jr. et al. |
| 2021/0077233 A1 | 3/2021 | Yancey et al. |

OTHER PUBLICATIONS

International Preliminary Report on Patentability in International Application No. PCT/US2022/042734 dated Jan. 29, 2024.
International Search Report and Written Opinion for International application No. PCT/US2021/057666 dated Feb. 3, 2022.
International Preliminary Report on Patentability in International Application No. PCT/US2021/057666 dated Dec. 16, 2022.

* cited by examiner

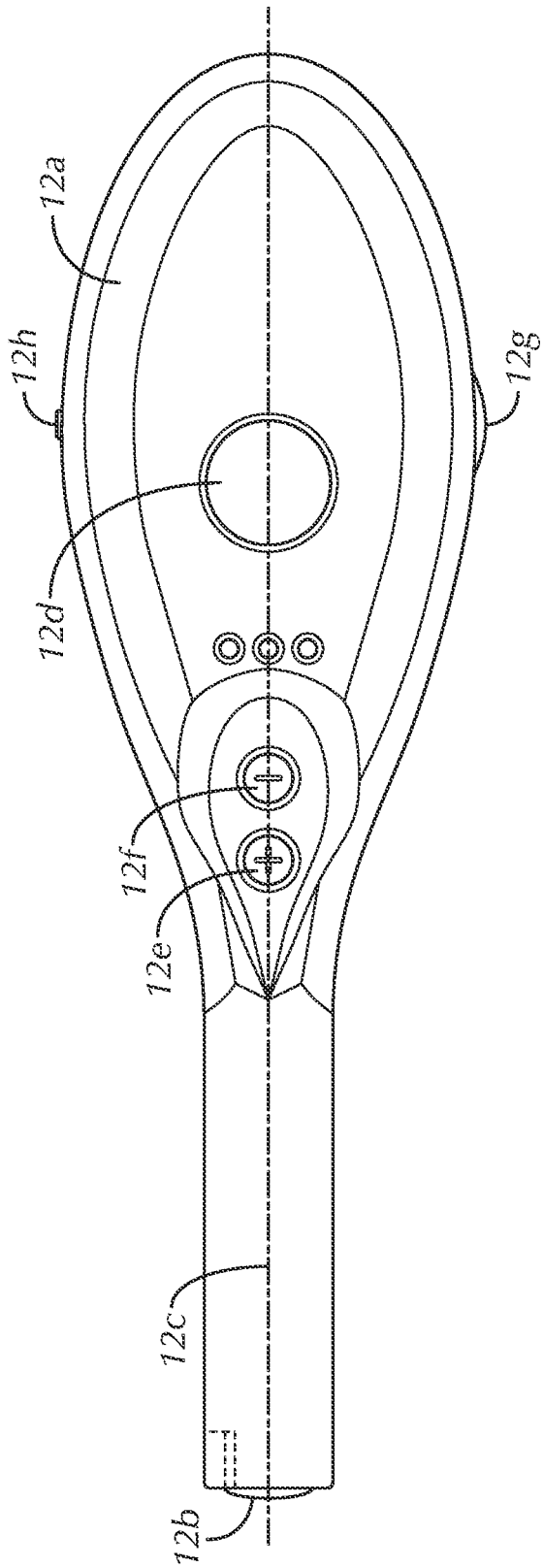
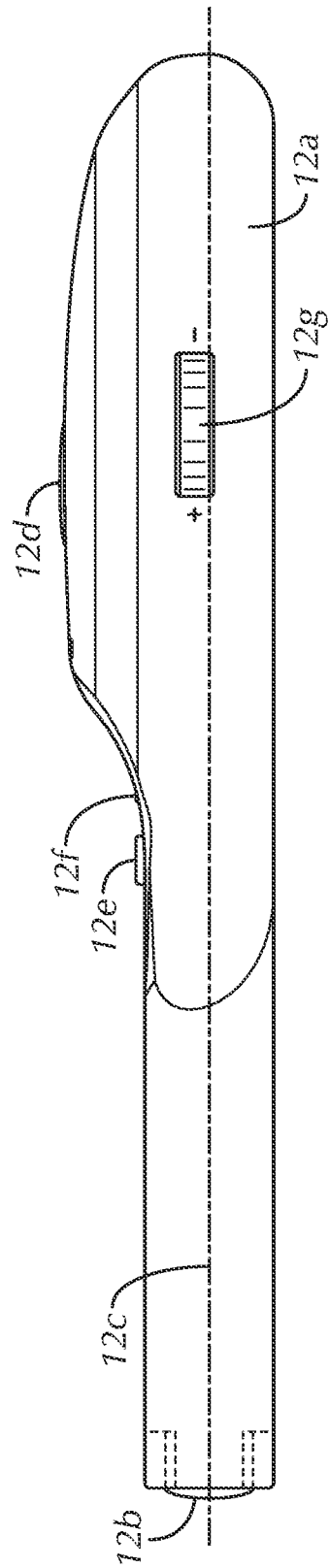
FIG. 7
FIG. 7A

DENTAL IMAGING SYSTEM AND METHOD

CROSS-REFERENCE TO RELATED APPLICATIONS

The present application is a continuation-in-part under 35 U.S.C. §§ 120, 363 and 365(c) of International Patent Application No. PCT/US22/42734, filed Sep. 7, 2022, which was published in English on Mar. 16, 2023 as International Patent Application Publication No. WO 2023/038954 and claims the benefit of U.S. Provisional Patent Application Nos. 63/241,367, filed Sep. 7, 2021; 63/286,299, filed Dec. 6, 2021; 63/449,187, filed Mar. 1, 2023 and 63/455,788, filed Mar. 30, 2023, each titled, "Digital Imaging System and Method," the entire contents of which are incorporated herein by reference in their entirety.

BACKGROUND OF THE INVENTION

There are many dental imaging devices, yet none provide a quick and consistent system and/or method of capturing buccal (external) images of the teeth and full arch lingual and/or occlusal views. External cameras are used to provide left, right and center buccal views, with the jaws open or closed. Intra-oral cameras typically are used to capture images of a particular tooth or multiple teeth but not full arch views. X-ray imaging systems are also utilized to provide images of the patient's teeth and arches, although such systems are typically relatively complicated, expensive, and cumbersome. However, both traditional camera and intra-oral cameras, as well as x-ray imaging systems, have the limitation as described more fully below.

Clinicians (dentists, dental assistants, etc.) benefit from the ability to see the full patient arch from what is commonly called the occlusal view. This means generally being able to see all teeth in a dental arch at once in either the mandibular or maxillary jaw. The occlusal views allow clinicians to see tooth and jaw alignment, tooth rotations, spacing between teeth, the chewing surface of the teeth, as well as a lingual view of some-or-all the teeth, gum tissue concerns, and otherwise assess a patient's oral health. However, this view is difficult to capture using current techniques and equipment.

Traditional cameras, capturing the images from outside the mouth, or intra-oral cameras shooting from inside the mouth, are not well-suited for this task. The difficulties are a result of several factors, including limited space in a patient's mouth, odd angles of the mouth, oddly shaped image capture devices, poor lighting, soft tissue blocking views of the teeth, and unsteady hands by the user. Additionally, humidity in the mouth causes fogging of camera lenses and/or reflecting mirrors that may be utilized to capture images from inside patient's mouth. Current techniques to capture these occlusal views typically involve one of two options, a) taking the picture using a mirror that is placed on the patient's tongue (or roof of their mouth) and angled such that the camera lens is focused on the mirror itself, thus providing a view of the patient's arch, or b) simply asking the patient to open their mouth as widely as they can and taking a picture of the arch. Both techniques have significant drawbacks. The first technique (using a mirror) is unwieldy, uncomfortable, inconsistent, prone to fogging, and susceptible to human error. The mirrors often fog-up, inconsistent sizing and angles of the photos make the photos susceptible to human error and commercially available medical quality mirrors are expensive. Additionally, the mirrors need to be sterilized after each use. The second technique (asking the patient to "open wide") has significant limitations, including views that are of poorly lighted or blurry, odd angles that make it difficult to determine depth of view, blocked views, and a host of human error problems.

The preferred invention provides a better way to capture occlusal and lingual views of the teeth due to its unique design and functionality, which addresses the shortcomings of the above-described prior art methods and devices. The preferred invention also preferably enables relatively consistent, high quality images to be taken from outside the patient's mouth, providing, center, left and right buccal views, as well as a panoramic full or partial mouth view. Images may be video or still. The preferred invention also facilitates monitoring dental appliances positioned in a patient's mouth, such as a palate expander or palatal expander. The imaging system and method may permit a patient to collect images of the palate or palatal expander at predetermined intervals to determine the amount of expansion that has occurred in the patient's mouth and whether the patient should schedule an appointment with their dentist.

The preferred invention addresses shortcomings of the prior art systems and methods utilizing an image capture device that consistently spaces the camera from the patient's teeth and arches utilizing a relatively simple system and method, particularly compared to prior art systems and methods.

BRIEF SUMMARY OF THE INVENTION

Briefly stated, the preferred invention is directed to a dental imaging system for capturing images of a patient's arches and teeth includes a central processor for storing images, a camera having a camera lens and a camera housing, and a camera holder having a tray, an angled column extending from a front of the tray and an engagement mechanism positioned at a distal end of the angled column. The engagement mechanism is configured to releasably engage the camera to orient the camera lens toward the patient's arches and teeth.

In another aspect, the preferred invention is directed to a camera system for capturing images of a patient's arches and teeth. The camera system includes a camera having a housing and a lens, and a camera holder having an engagement mechanism, an angled column and a positioning block. The engagement mechanism is connected to a distal end of the angled column and the positioning block is connected to a proximal end of the angled column. The engagement mechanism is configured for releasably mounting the camera. The camera lens is oriented toward the distal end in a mounted configuration and the positioning block is configured to contact the patient's arches, teeth, cheeks or lips when collecting images with the camera.

In an additional aspect, the preferred invention is directed to a method for capturing images of a patient's arches and teeth with a camera defining a camera axis and a camera holder having a positioning block and an engagement mechanism defining an engagement mechanism axis. The method includes engaging the camera with the engagement mechanism, retracting the patient's lips or cheeks to expose a desired area of the patient's teeth, engaging the positioning block with the patient's teeth, arches, lips or cheeks proximate a desired area of the patient's teeth, orienting the camera axis to intersect the desired area, acquiring an image of the desired area with the camera, and transmitting the acquired image to a central processor. The camera and the camera holder are pivotable relative to the patient's teeth, arches, lips or cheeks about the positioning block.

In a further aspect, the preferred invention is directed to a method for capturing images of a patient's arches and teeth with a camera defining a camera axis. The method includes receiving, from a central processor, instructions regarding a desired area of the patient's arches and teeth, retracting the patient's lips or cheeks to expose the desired area, orienting the camera such that the camera axis intersects the desired area, receiving, from the central processor, instructions regarding orienting or spacing the camera relative to the desired area, acquiring an image of the desired area with the camera, transmitting the acquired image to the central processor, and receiving, from the central processor, instructions regarding acceptance or rejection of the acquired image.

The preferred invention includes an image capture device or system which also can be used with an optional positioning device.

BRIEF DESCRIPTION OF THE SEVERAL VIEWS OF THE DRAWINGS

The foregoing summary, as well as the following detailed description of preferred embodiments of the dental imaging system and method, will be better understood when read in conjunction with the appended drawings. For the purposes of illustrating the preferred dental imaging system and method, there are shown in the drawings preferred embodiments. It should be understood, however, that the system and method are not limited to the precise arrangements and instrumentalities shown. In the drawings:

FIG. 7 is a top plan view of a camera in accordance with a preferred embodiment of the present invention;

FIG. 7A is a side elevational view of the camera of FIG. 6;

DETAILED DESCRIPTION OF THE INVENTION

Figure 1:
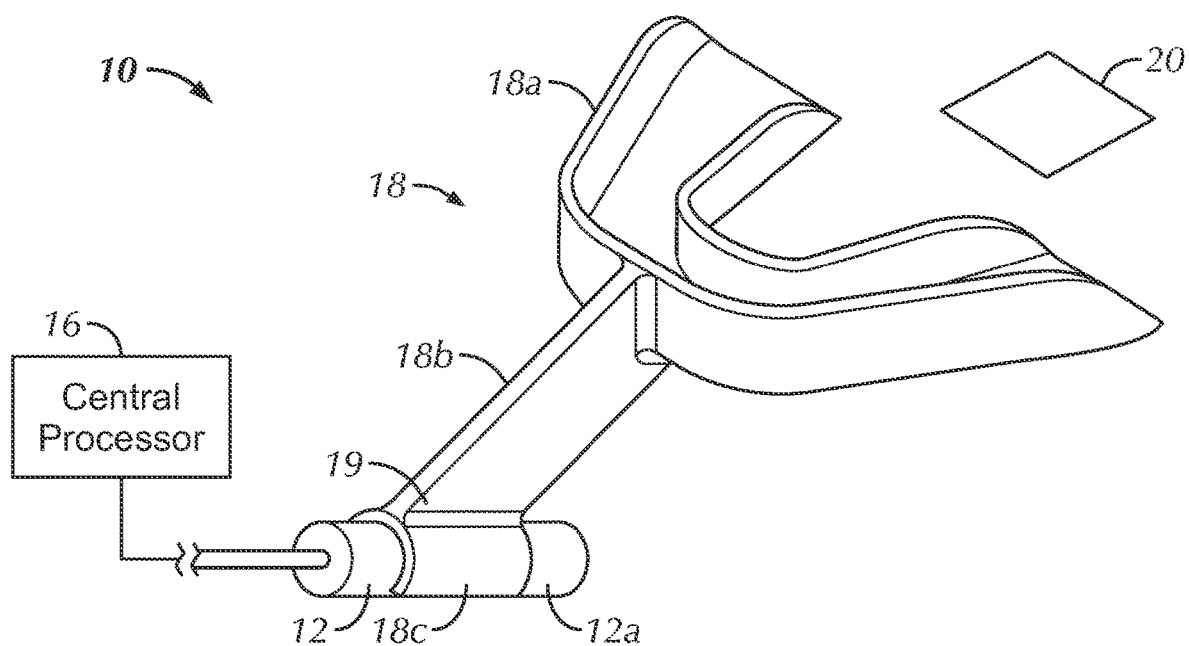
FIG. 1 illustrates a top perspective of a first preferred camera holder and a camera for use with a preferred dental imaging system.

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred dental imaging system and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit. In addition, the headings utilized herein are for reference purposes only and are not intended to impact the scope, meaning or interpretation of the present disclosure.

Image Capture Device

Referring to FIGS. 1-9, a preferred dental imaging system, generally designated 10, 10', 10", 10''', 10'''', 10''''', 10'''''' includes a camera 12, a power and data cord 14, a central processor 16, and a camera holder 18, 18', 18", 18''', 18'''', 18''''', 18''''''.

Figure 1A:
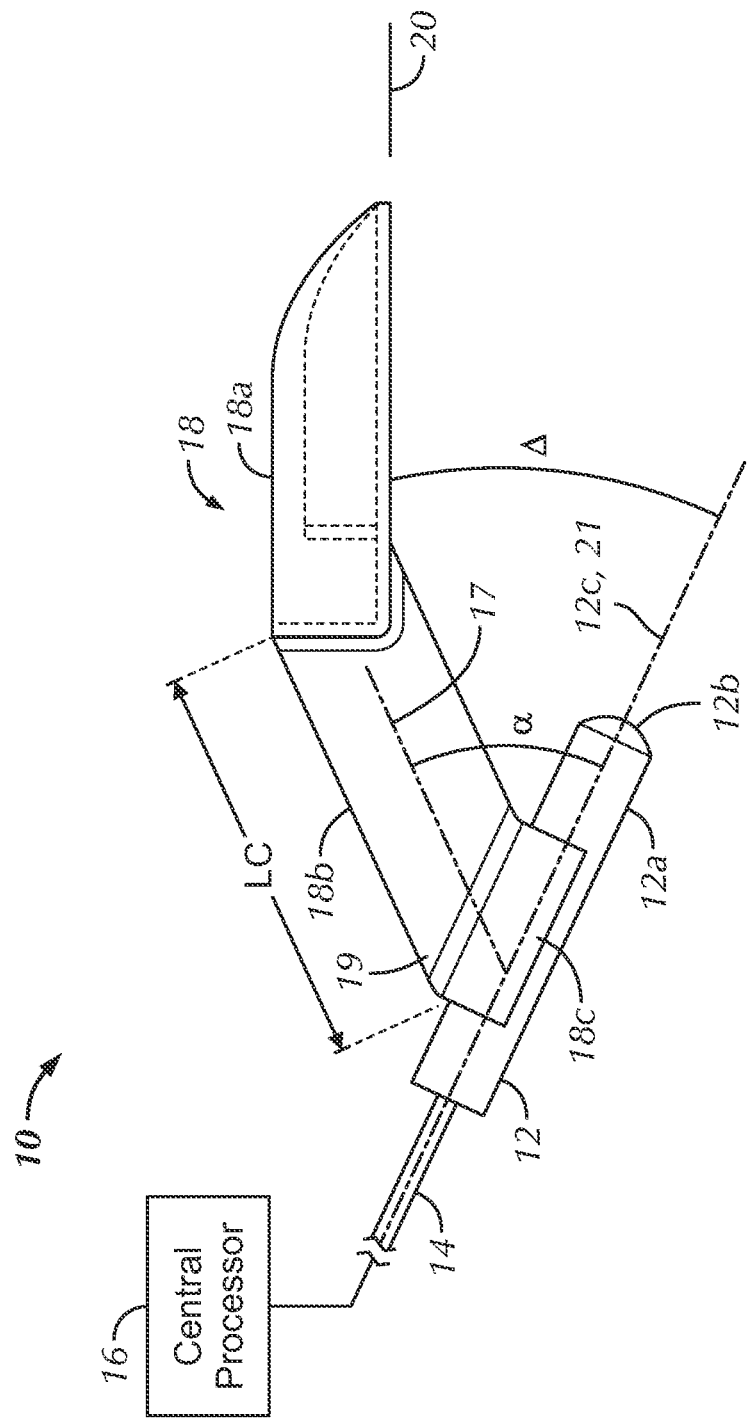
FIG. 1A illustrates a side elevational view of the camera holder and camera of FIG. 1.

Referring to FIGS. 1 and 1A, the preferred camera 12 includes a camera lens 12b housed in a generally tubular shaped housing 12a. The housing 12a connects to the central processor 16, which may include an image processor, through the power and data cord 14. The housing 12a of the preferred embodiment has a generally cylindrical shape with the data cord 14 extending from an end opposite the lens 12b. The camera 12 is not limited to having the cylindrical shape with the data cord 14 and may be comprised of a camera in a smartphone 100 that is connected to the camera holder 18, 18', 18", 18''', 18'''', 18''''', 18'''''' for acquiring images or another camera for capturing images. The camera 12 may be comprised of the camera of a smartphone 100 in any of the systems, applications and methods described herein. The smartphone 100 preferably includes a display and the central processor 16 may send instructions for presentation on the display or the processor of the smartphone 100 may be employed as the central processor 16. The instructions may include the desired areas of the patient's teeth and/or arches and instructions regarding orienting or spacing the camera 12 relative to the desired area, which may be presented on the display. The display may present the desired area to the patient to preview the desired area before the images are acquired. The orienting and spacing instructions may include a desired number of images, wherein the desired area is comprised of a plurality of desired areas. The central processor 16 may also include a user interface or may be comprised of a smartphone 100, tablet, memory storage device, desktop computer or any component that may collect and store the images taken by the camera 12. The power and data cord 14 may alternatively not be used and the image capture device or camera 12 may be connected to the central processor 16 wirelessly or via a wireless protocol, such as Bluetooth. The camera 12 and associated lighting may be powered by a local power source at the camera 12, such as a battery, or may be powered by the central processor 16 through the power and data cord 14, such as by a rechargeable battery of the central processor 16. The central processor 16 may be comprised of a mobile phone, tablet or other powered processor. The preferred dental imaging system 10, 10', 10", 10''', 10'''', 10''''', 10'''''' and, specifically, the camera 12 is preferably configured to capture the desired images either manually or automatically. For example, the user may prompt collection of an image or video by manually operating an image signal using the central processor 16, which sends a signal to the camera 12 to capture an image, or the camera 12 may automatically take an image based on alternative prompts related to the dental imaging system 10, 10', 10", 10''' such as the camera 12 being appropriately positioned relative to the patient's teeth or arches such that image capture is triggered.

Figure 6:
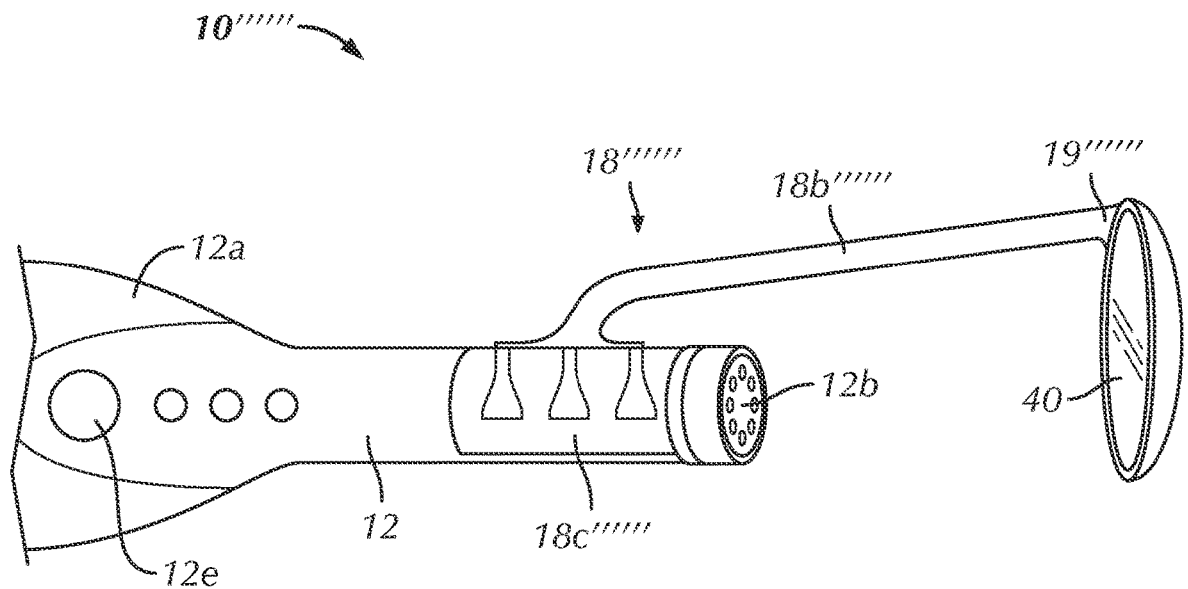
FIG. 6 is a top plan view of a seventh preferred camera holder for capturing images of the patient's teeth and/or arches.
Figure 8:
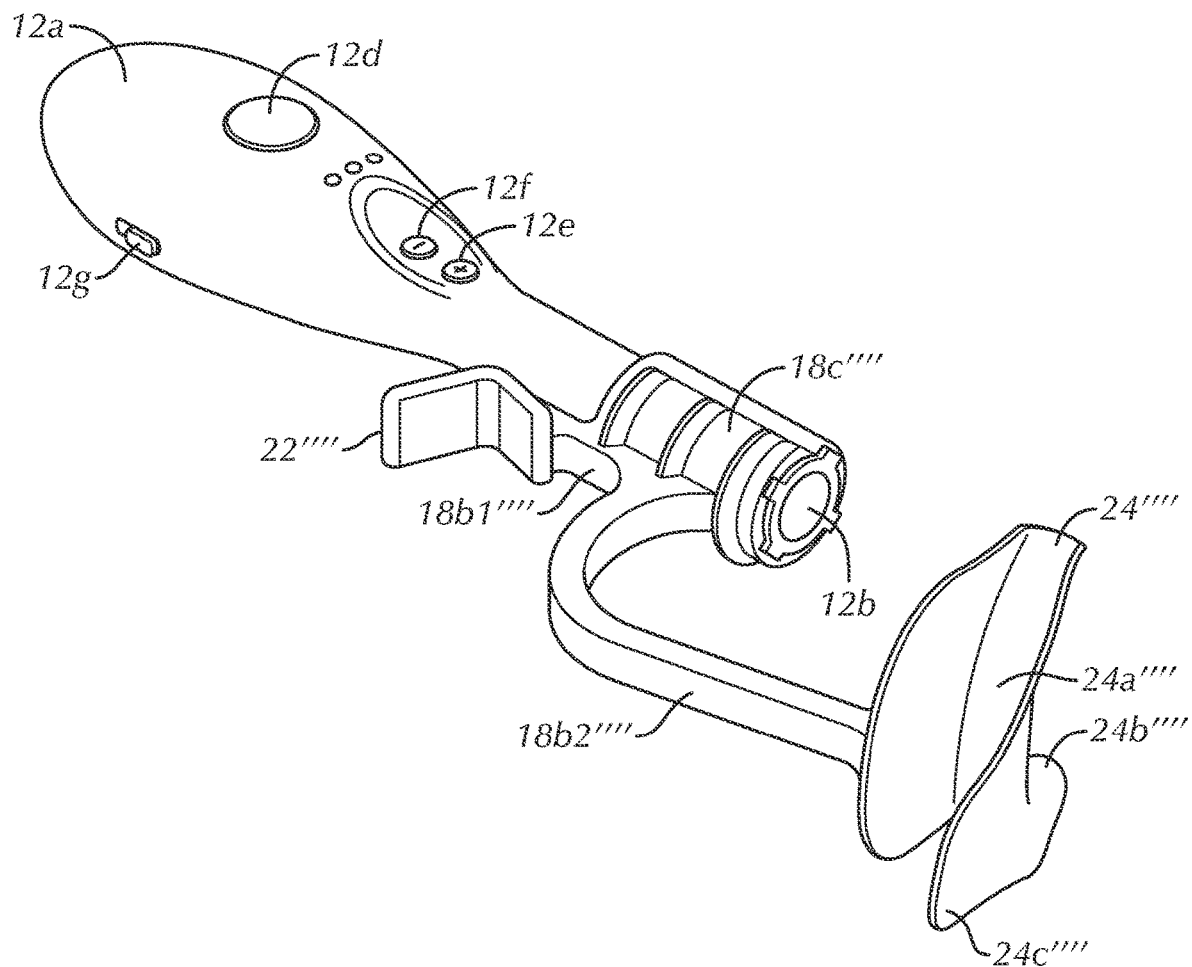
FIG. 8 is a top perspective view of the preferred camera of FIG. 6 connected to the fifth preferred camera holder of FIG. 5.

Referring to FIGS. 6-8, the camera 12 may be comprised of a wireless camera 12 with a capture button 12d, a zoom in button 12e and a zoom out button 12f. The wireless camera 12 enables image capture with a single hand by holding the camera 12 and depressing the capture button 12d. The patient may position the camera 12 and dental imaging system 10 with a single hand, zoom in or zoom out on the desired area with the zoom in and zoom out buttons 12e, 12f, and capture the image by depressing the image capture button 12d, all with a single hand. The wireless camera 12 also preferably includes a light emitting diode ("LED") button 12g that illuminates or turns off illuminating elements or lights to illuminate the desired area of the patient's teeth and/or arches. The wireless camera 12 further preferably includes an on/off button 12h to turn the camera 12 off or on, respectively.

Figure 2:
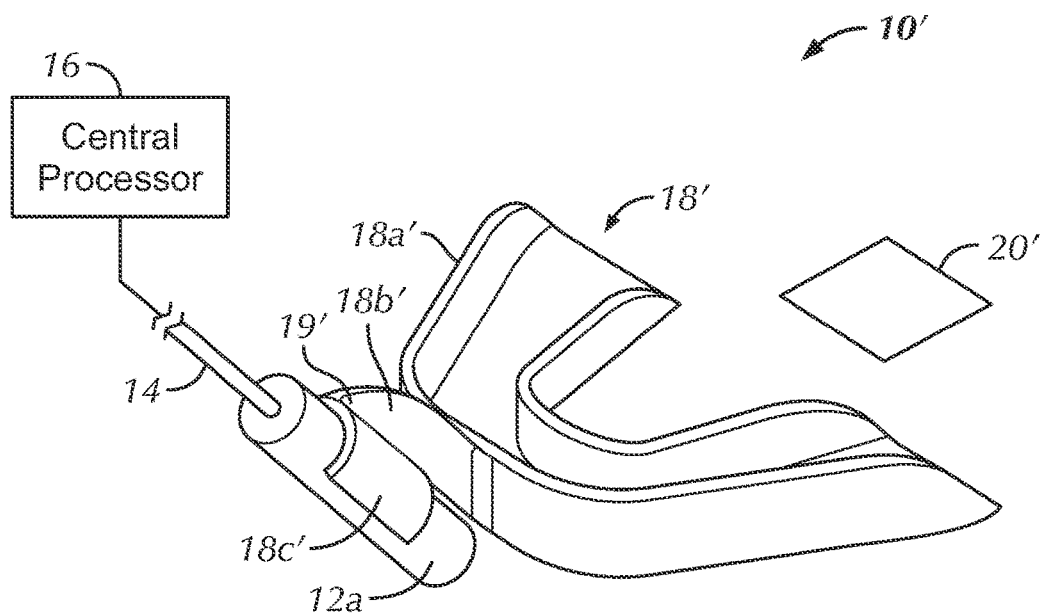
FIG. 2 illustrate top perspective view of a second preferred camera holder and a camera for use with a preferred dental imaging system.
Figure 2A:
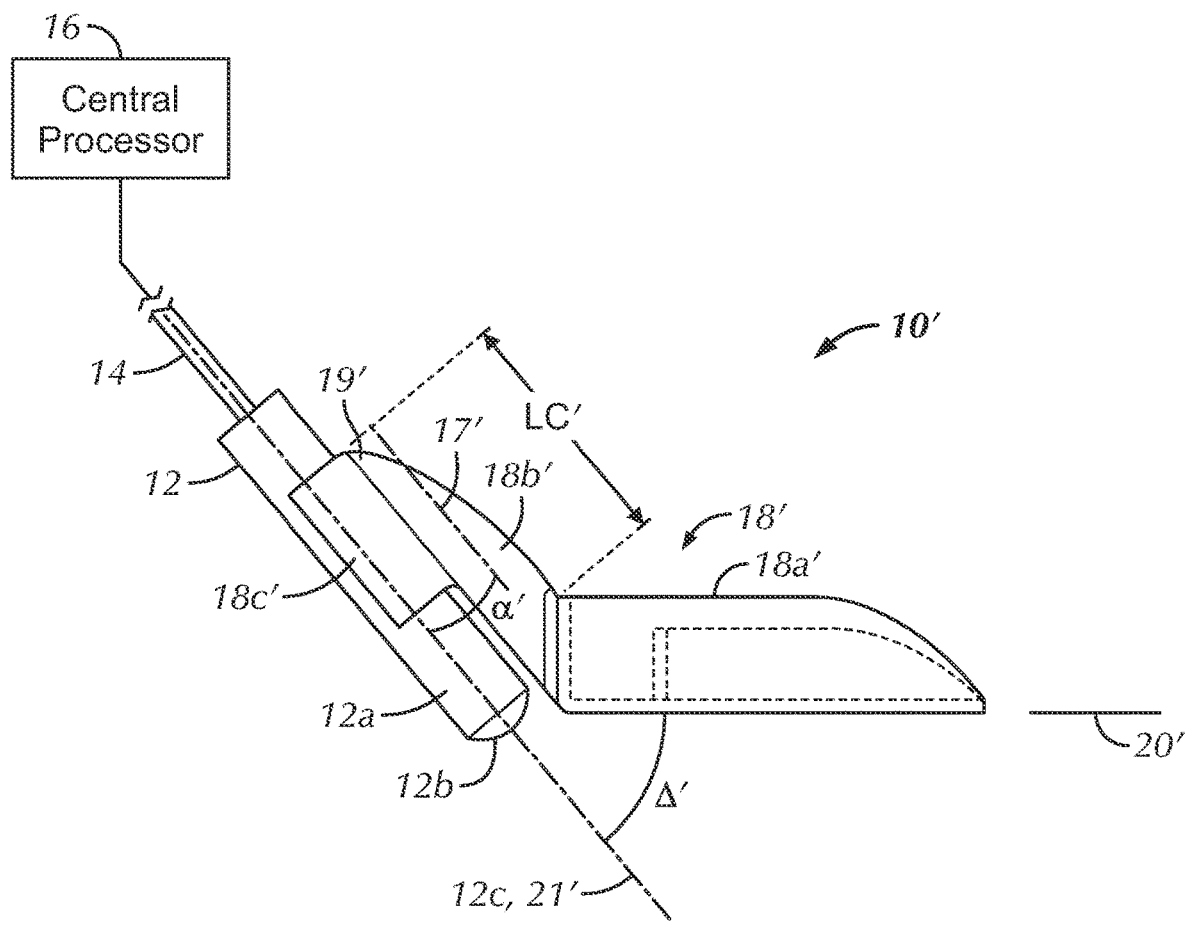
FIG. 2A illustrates a side elevational view of the camera holder and camera of FIG. 2.

Referring to FIGS. 1-2A, the preferred dental imaging system 10 also includes first and second preferred embodiments of a camera holder 18, 18' that holds the camera 12 and orients the camera 12 relative to the patient's mouth to capture the desired images. The camera holders 18, 18' in accordance with first and second preferred embodiments are shown in FIGS. 1-2A with the same reference numerals utilized to identify similar or the same features and a prime symbol (') utilized to distinguish the features of the second preferred embodiment of the camera holder 18' from the features of the first preferred embodiment of the camera holder 18. The preferred camera holder 18, 18' includes a tray 18a, 18a', an angled column 18b, 18b', and an engagement mechanism 18c, 18c' connected to a distal end 19, 19' of the angled column 18b, 18b'. The engagement mechanism 18c, 18c' is preferably designed and configured to engage and hold the camera 12 relative to the tray 18a, 18a' for collecting images of the patient's mouth and teeth. The first and second preferred engagement mechanisms 18c, 18c' are configured to releasably mount the camera 12 by clamping the camera 12 but are not so limited and the engagement mechanisms 18c, 18c' may otherwise releasably engage or mount the camera 12, such as by fastening, clamping, snap locking, adhesive bonding, hook and loop material or other releasable mounting systems or techniques. In addition, the engagement mechanism 18c, 18c' is not limited to releasably engaging or mounting the preferred camera 12 and the camera 12 may be integrally attached or mounted to the engagement mechanism 18c, 18c' and the angled column 18b, 18b' or the housing of the camera 12 may be integrally formed with the angled column 18b, 18b' and the engagement mechanism 18c, 18c'. The engagement mechanisms 18c, 18c' may also be designed and configured to mount an alternative camera, such as a smartphone 100 and direct the field of view of the smartphone camera toward the patient's teeth and arches.

In the first and second preferred embodiments, the tray 18a, 18a' defines a base plane 20, 20' and the camera 12 defines a camera axis 12c. When the camera 12 is positioned in and secured by the engagement mechanism 18c, 18c', the base plane 20, 20' and the camera axis 12c define a camera angle $\Delta$, $\Delta'$. In the first and second preferred embodiments, the camera angle $\Delta$, $\Delta'$ is approximately twenty to fifty-five degrees (20-55°), more preferably twenty-five to fifty degrees (25-50°). In the first preferred embodiment, the camera angle $\Delta$ is approximately twenty-five degrees (25°) and in the second preferred embodiment, the camera angle $\Delta'$ is approximately fifty degrees (50°). The first and second preferred embodiments of the camera holder 18, 18' are designed and configured for capturing occlusal images of the patient's teeth and arches.

Referring to FIGS. 1-4B, the preferred engagement mechanisms 18c, 18c' are comprised of a C-shaped clamp that clamps the camera 12 in the mounted configuration but are not so limited. The engagement mechanism 18c, 18c' may be comprised of a fastening mechanism, clamp, snap-lock, adhesive bonding, hook and loop material or alternative system or method that secures the camera 12 to the angled column 18b, 18b'. Alternatively, the engagement mechanism 18c, 18c' may be integrally formed with the camera housing 12a to connect the camera 12 to the angled column 18b, 18b'. The angled column 18b, 18b' preferably extends at or along a column axis 17 away from the engagement mechanism 18c, 18c'. The column axis 17 and the camera axis 12c define a column angle α, α', α", α'" that is approximately zero to forty-five degrees (0-45°) but is not so limited and may have nearly any angle, such that the lens 12b is oriented toward the desired target area of the patient's teeth and arches in the operating configuration or during use. As non-limiting examples, the column angle α of the first preferred embodiment is approximately forty-five degrees (45°), the column angle α' of the second preferred embodiment is approximately zero degrees (0°), the column angle α" of the third preferred embodiment is approximately thirty degrees (30°) and the column angle α'" of the fourth preferred embodiment is approximately thirty degrees (30°).

The engagement mechanisms 18c, 18c', 18c", 18c'" of the preferred embodiments define an engagement mechanism axis 21, 21', 21", 21'" that is substantially coaxial with the camera axis 12c when the camera 12 is mounted to the engagement mechanisms 18c, 18c', 18c", 18c'". The preferred angled columns 18b, 18b', 18b", 18b'" have a column length LC. The column length LC, LC', LC", LC'" of the preferred embodiments is approximately thirty to forty millimeters (30-40 mm) but is not so limited and may be shorter or longer depending on the shape, size and configuration of the camera holder 18, 18', 18", 18'", the configuration of the camera 12 and other factors related to the design and configuration of the system. The angled columns 18b, 18b', 18b", 18b'" also preferably have a cross-sectional shape that may be circular, rectangular, square or nearly any other shape that is able to withstand the normal operating conditions of the camera holder 18, 18', 18", 18'", take on the general size and shape of the camera holder 18, 18', 18", 18'" and perform the preferred functions of the angular columns 18b, 18b', 18b", 18b'". The camera holder 18, 18', 18", 18'" may also include a mirror attached to the distal end 19, 19', 19", 19'" of the angled column 18b, 18b'", the positioning block 22", 22'", or other areas of the camera holder 18, 18', 18", 18'", preferably to collect lingual and/or occlusal views of the patient's teeth and arches wherein the camera axis 12c intersects the mirror to acquire images from the face of the mirror.

Referring to FIG. 6, a sixth preferred dental imaging system 10""" includes a camera holder 18""" that holds the camera 12 and orients the camera 12 relative to the patient's mouth to capture the desired images, which are preferably lingual and/or occlusal images. The camera holder 18""" in accordance with the sixth preferred embodiment is shown in FIG. 66 with the same reference numerals utilized to identify similar or the same features when compared to the first, second, third, fourth and fifth preferred camera holders 18, 18', 18", 18'", 18"" and a five prime symbols (""") utilized to distinguish the features of the sixth preferred embodiment of the camera holder 18""" from the features of the first, second, third, fourth and fifth preferred embodiments of the camera holder 18, 18', 18", 18'", 18"". The seventh preferred camera holder 18"""" includes a mirror 40 attached to the distal end 19"""" of the angled column or arm 18b"""". The seventh preferred camera holder 18"""" facilitates collection of lingual and/or occlusal images of the patient's teeth and/or arches by placing the mirror 40 in the patient's mouth and collecting the image from the reflection in the mirror 40. The central processor 16 may direct the user regarding the positioning of the mirror 40 for capturing the images. The mirror 40 is particularly configured to collect lingual images of the patient's teeth but is not so limited and may be designed and configured to collect or acquire nearly any images of the patient's teeth that may be collected via reflection of the desired area from the face of the mirror 40.

Image Capture

Capturing images with the preferred dental imaging system 10, 10', 10", 10'", 10"", 10""", 10"""" may be accomplished by using a single lens 12b or with multiple lenses 12b on the camera 12. In the preferred embodiments a single lens 12b is used but is not so limiting. The camera 12 may be comprised of multiple cameras having multiple lenses for capturing the desired images of the patient's arches. In the preferred embodiments, the camera lens 12b has the following non-limiting characteristics, although the lens 12b may have alternative characteristics without significantly impacting the design, operation and configuration of the lens 12b—resolution: 1944 high-definition ("HD") and focal length of two and seventy-six hundredths to fifteen and seven tenths inches (2.76-15.7").

An alternative embodiment of the dental imaging system 10, 10', 10", 10'", 10"", 10""", 10"""" may include multiple lenses on the camera 12, with one or more lenses angled to enhance resolution and expand the field of view.

Figure 15:
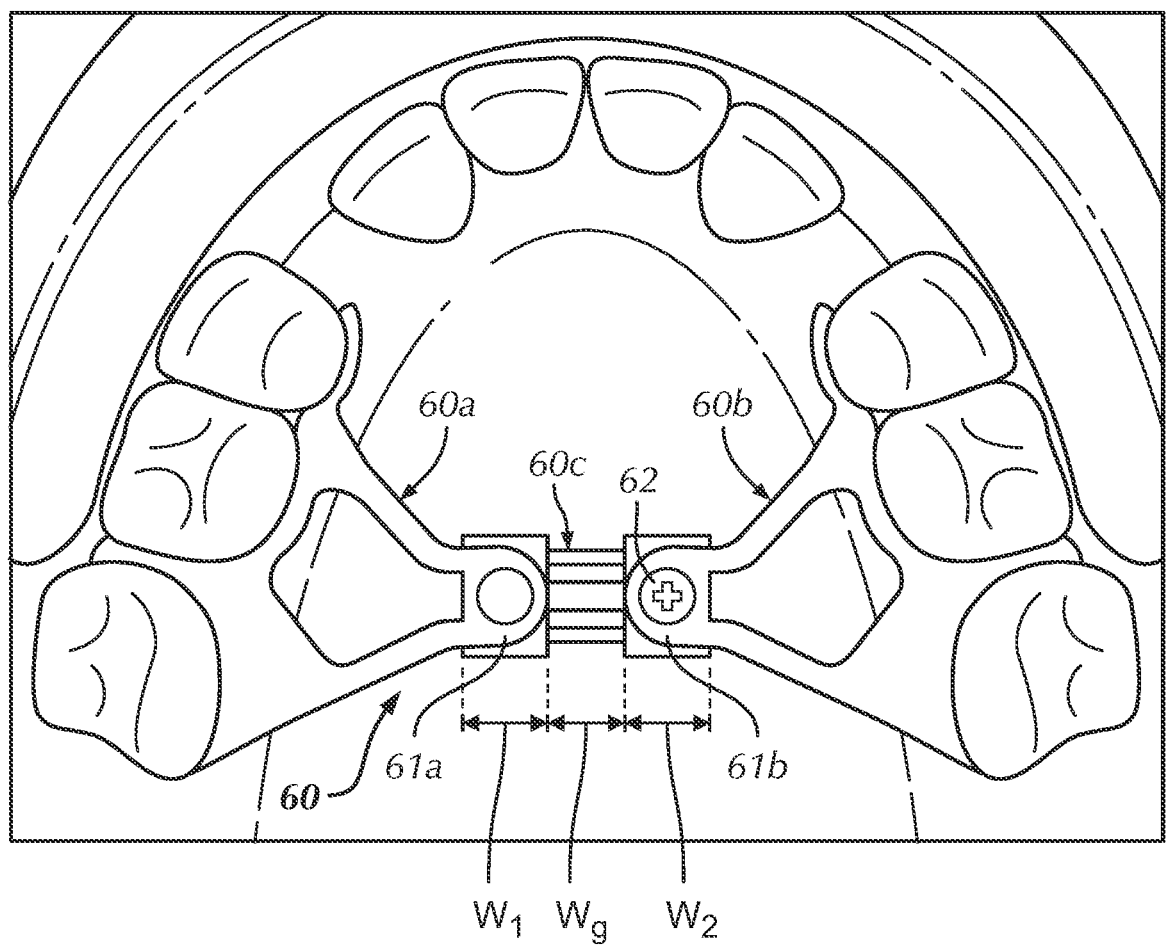
FIG. 15 is an occlusal view of a patient's upper arch with a palate expander mounted to a plurality of the patient's molars.

The dental imaging systems 10, 10', 10", 10'", 10"", 10""", 10"""" may be utilized to monitor or evaluate a palate or palatal expander 60 and the impact of the palate expander 60 on the patient's arches and teeth. Capturing the occlusal view of the mandibular or maxillary arches is preferred for monitoring the status of the palatal expander 60—how much expansion has been achieved, how many "turns of the screws" have been done and remain to be done, etc. The dental imaging systems 10, 10', 10", 10'", 10"", 10""", 10"""" may be utilized to evaluate whether the palatal expander 60 is seated/fitted properly, etc. Referring specifically to FIG. 15, the palatal expander 60 includes first and second side arms 60a, 60b and a central support 60c. A screw 62 is connected to the central support 60c and may be actuated or turned to urge the first and second side arms 60a, 60b toward or away from the central support 60c. Collecting images with the dental imaging systems 10, 10', 10", 10'", 10"", 10""", 10"""" may be utilized to monitor or evaluate the palatal expander 60 and the patient's arches to determine how much movement has been achieved by the palatal expander 60 and whether the palatal expander 60 is properly mounted to the patient's teeth and remains properly mounted to the patient's teeth, without constantly requiring in-person patient visits to a dental professional, thus saving time and inconvenience for the patient and the dental professional.

In operation, the system utilizes a method for capturing images of a patient's arches and teeth with a camera 12 defining a camera axis 12c and a camera holder 18, 18', 18", 18'" having a positioning block 22", 22'" and an engagement mechanism 18c, 18c', 18c", 18c'" defining an engagement mechanism axis 21, 21', 21", 21'". The user or a clinician engages the camera 12 with the engagement mechanism 18c, 18c', 18c", 18c'" to secure the orientation of the camera 12 relative to the engagement mechanism 18c, 18c', 18c", 18c'" and the orientation of the field of view of the camera 12 relative to the engagement mechanism 18c, 18c', 18c", 18c'". The user or clinician is not limited to engaging the camera 12 with the engagement mechanism 18c, 18c', 18c", 18c'", as the camera 12 may be integrally secured to or formed with the angled column or arm 18b, 18b', 18b", 18b'". In the preferred embodiments, the camera 12 is engaged by the engagement mechanism 18c, 18c', 18c", 18c'" by clamping or snap-fitting the camera 12 with the engagement mechanism 18c, 18c', 18c", 18c'", but is not so limited and the camera 12 may be otherwise secured to the engagement mechanism 18c, 18c', 18c", 18c'" such as by adhesive bonding, fastening, integrally forming, or otherwise securing the camera 12 to the engagement mechanism 18c, 18c', 18c", 18c'". The camera axis 12c is preferably coaxial with the engagement mechanism axis 21, 21', 21", 21'" when the camera 12 is engaged by the engagement mechanism 18c, 18c', 18c", 18c'". The camera 12 is not limited to being clamped by the engagement mechanism 18c, 18c', 18c", 18c'" and may be engaged by the engagement mechanism 18c, 18c', 18c", 18c'" via fastening, adhesive bonding, clamping, snap locking, bayonet engagement, or related securing or mounting systems or methods.

During operation, the patient or a clinician, preferably the patient, retracts the patient's lips or cheeks to expose a desired area of the patient's teeth wherein the desired images are taken. The patient may be directed by prompts sent from the central processor 16, written instructions, or other prompts from a clinician, dentist, orthodontist, or doctor to select desired areas, sequence the images that are taken, determine if the images are acceptable, and other instructions so that the appropriate desired images are collected. The patient's lips and/or cheeks are preferably retracted by the camera holder 18, 18', 18", 18'", but are not so limited and may be retracted by other instruments, such as a tissue retractor, the soft tissue retractor 26, the patient or clinician manually, or by other systems and methods. The user preferably collects or acquires the images based on the instructions from the central processor 16, wherein the images may be comprised of left, right and center buccal areas, but are not so limited and may be comprised of nearly any images that are desired by the clinician, user, or other healthcare professional. The desired areas may also be comprised of a lingual area of the patient's teeth, which images may be acquired by incorporating the mirror 40 into the camera holder 18, 18', 18", 18'" that is intersected by the camera axis 12c to reflect the image of the desired area onto the lens 12b. The desired area may alternatively be comprised of center, left, and right buccal areas of the patients teeth and/or arches. Alternatively, the desired area may be comprised of an occlusal view of a patient's mandibular or maxillary arches. The central processor 16 may determine how much expansion has been achieved through the palatal expander 60 based on comparison of the acquired image to a previously acquired image via observing literal movement or by determining the number of turns made with the screw 62 or key of the expander 60.

In the preferred process, the positioning block 22", 22'" is engaged with the patient's teeth, arches, lips, or cheeks proximate a desired area of the patient's teeth or arches. The camera 12 and the camera holder 18, 18', 18", 18'" are pivotable relative to the patient's teeth, arches, lips or cheeks about the positioning block 22", 22'" to orient camera 12 and the camera axis 12c toward the desired area for image capture and, preferably, the camera axis 12c is oriented to intersect the desired area. The user or clinician actuates the camera 12 to acquire the image of the desired area. The desired images are subsequently transmitted to the central processor 16. The acquired images may be transmitted to the central processor 16 via the data cord 14 via wired transmission protocol or via wireless protocols.

The central processor 16 may analyze the received images from the camera 12 and transmit acceptance or rejection of the acquired images to the camera 12. The camera 12 receives the acceptance or rejection and the user or clinician is directed to terminate acquisition of images, re-take images that were rejected, collect additional images based on the analysis of the central processor 16, or otherwise act based on the instructions from the central processor 16.

The central processor 16 preferably includes dental and/or medical history of the patient prior to receipt and acquisition of the images. The central processor 16 may include an expected number of teeth in the desired area and may compare the expected number of teeth to a number of teeth in the acquired image(s) when analyzing the collected image(s). The central processor 16 may send a message to the patient and/or clinician regarding the comparison of the expected number of teeth and the number of teeth in the acquired image. This comparison may be utilized to identify lost or missing teeth, check whether the desired image(s) captured the correct desired area, and other analysis that may be conducted based on this comparison.

Palate Expander

Once the images of the patient's arches are collected, the collected images may be utilized to monitor and evaluate the palate expander 60. The collected images may specifically be utilized to determine the amount of movement of the patient's teeth and palate by visually comparing the collected images and/or the number of key turns of the screw 62. The following general formula calculates the number of key turns for any given palatal expander:

key turns=(current gap−initial gap)÷increase per key turn

Measuring the physical expansion of a width of a gap for the palatal expander 60 is constantly monitors by frequent, time-consuming patent in-person appointments and the preferred system and method may be utilized to approximate the expansion of the gap using the preferred system and method. In order to establish a proper scale, sizes of first and second reference blocks 61a, 61b connected to the first and second arms 60a, 60b of the palatal expander 60 are determined and stored in the central processor 16, as they have a fixed width. Block widths $W_1$, $W_2$ of the reference blocks 61a, 61b are determined in the collected image and the average block width W is stored in the central processor 16. The average block width W of the blocks 61a, 61b is compared to the stored block widths $W_1$, $W_2$ in order to obtain scaling information for the collected image. By determining the average block width W of the blocks 61a, 61b, this will aid in eliminating distortions that may be caused by odd angles of the lens during image capture, thus ensuring better accuracy. It is possible to do the same below calculations by measuring a single one of the reference blocks 61a, 61b (or any other fixed point or feature on the palate expander 60. Using this information, a gap width Wg measured between the first and second reference blocks 61a, 61b is then determined utilizing the images collected in the central processor 16 and applying the proper scale.

The following steps may be utilized calculate the approximate gap width Wg of the gap for the palate expander 60:

(0.5(measured block a+measured block b))÷x=real block size     1.

With this formula a value of "x" is established which allows us to convert our measurements to the proper scale. The average block width W of the blocks 61a, 61b comprised of the average of the first and second block widths $W_1$, $W_2$ is utilized to give us a more reliable value for "x".

Measured gap÷x=current gap    2.

With this formula, the previously calculated "x" is utilized to determine the current gap width Wg, which is then plugged into the following formula to calculate the number of key turns.

Having calculated the gap width Wg, the central processor 16 may solve for the number of key turns using the initial general formula. The following step calculates the approximate number of key turns:

(current gap−2.8)÷0.2=key turn    1.

the number of key turns is thereby calculated.

An example, but non-limiting scenario for a particular patient may include the following:
- an initial gap width Wg is 2.8 mm
- a final gap width Wg is 12 mm
- the palate expander 60 received 46 key turns of the screw 62
- therefore the gap width Wg increases by approximately 0.2 mm per key turn
- the first and second block widths are 4.5 mm
- the image for the first width $W_1$ of the first block 61a is measured at 5.9 mm
- the image for the second width $W_2$ of the second block 61b measured at 6.1 mm
- The image for the gap width Wg is measured at 12 mm real block size=(0.5(measured block a+measured block b))÷x 4.5=(0.5(8.9+9.1))÷x 4.5=(5(18))÷x 4.5=9÷x 4.5x=9

X=9÷4.5

X=2 current width=measured gap image÷x current width=12÷2 current width=6 key turns=(current width−initial width)÷increase per key turn key turns=(6−2.8)÷0.2 key turns=3.2÷0.2 key turns=16

Lighting

The dental imaging system 10, 10', 10", 10''', 10'''', 10''''', 10'''''' may include one or more lights or light sources, such as light emitting diode ("LED") (or comparable) lights, to illuminate the desired target areas for producing clear and consistent images. The light source illuminates the desired target areas when the images are acquired. The preferred system 10, 10', 10", 10''', 10'''', 10''''', 10'''''' may have a light adjustment feature (either manual or automatic or it may have an auto-flash feature). The light source is preferably connected to the camera holder 18, 18', 18", 18''', 18'''', 18''''', 18'''''' and/or the camera 12. The light source is configured to emit light along the camera axis 12c proximate the positioning block 22", 22''', the tray 18a, 18a', the positioning arm 24", or generally onto the desired area of the patient's teeth and/or arches to illuminate the patient's arches and/or teeth for image capture. The light source can include alternative light spectrums, a variety of colors in the visible spectrum, ultraviolet ("UV") and non-visible light spectrum. Such lights can help a clinician (can be human or computer) identify and/or measure a variety of bacteria (oral biomes) in an area of the mouth, gums, or throat (including streptococcal pharyngitis). The light source may also be attachable to the camera 12, preferably in a ring shape proximate the lens 12a that creates a wider circumference area to shine the light onto the desired or target area.

Buccal Imaging

Figure 3:
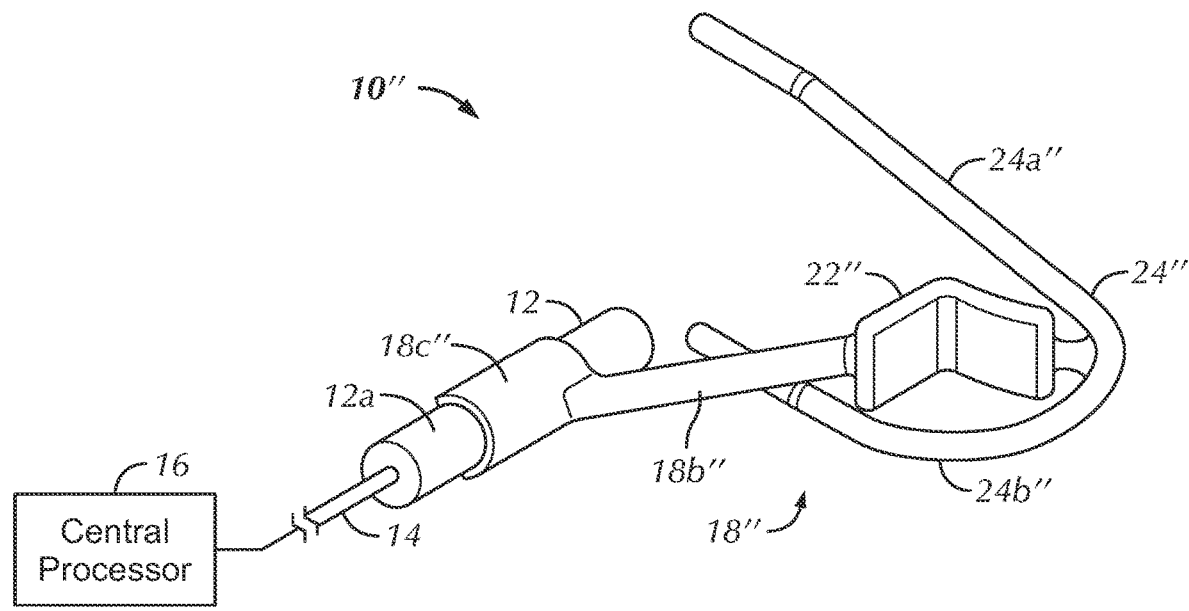
FIG. 3 illustrates a top perspective view of a third preferred camera holder and a camera for use with a preferred dental imaging system.
Figure 3A:
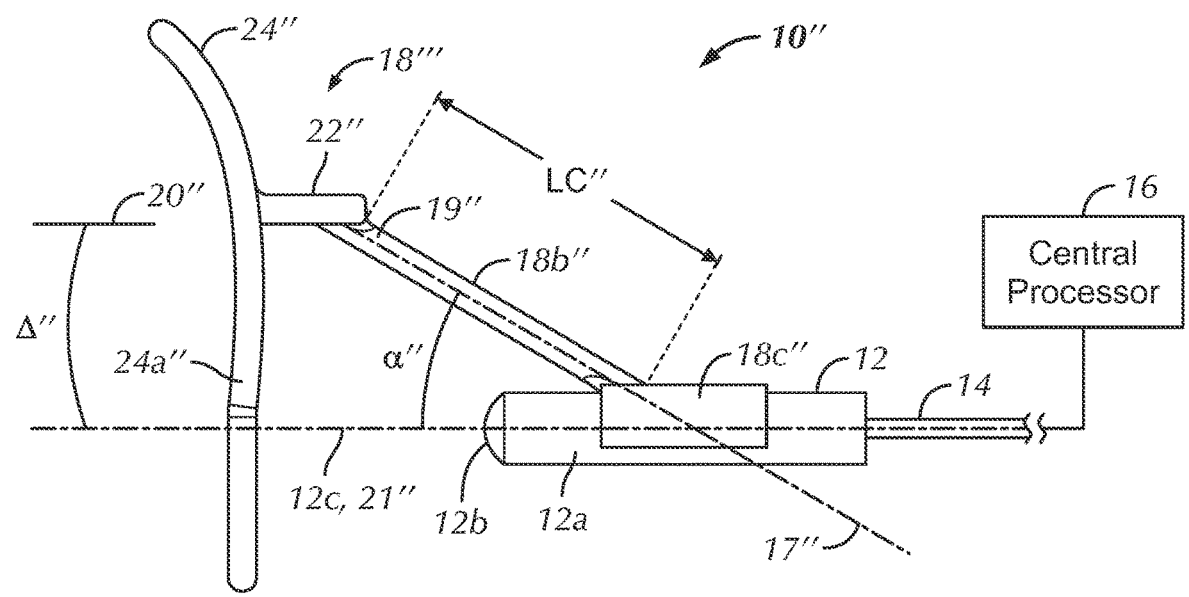
FIG. 3A illustrates a side elevational view of the camera holder and camera of FIG. 3.

Referring to FIGS. 3 and 3A, a third preferred dental imaging system 10" includes a camera holder 18" that holds the camera 12 and orients the camera 12 relative to the patient's mouth to capture the desired images, which are preferably buccal images. The camera holder 18" in accordance with the third preferred embodiment is shown in FIGS. 3 and 3A with the same reference numerals utilized to identify similar or the same features when compared to the first and second preferred camera holder 18, 18' and a double prime symbol (") utilized to distinguish the features of the third preferred embodiment of the camera holder 18" from the features of the first and second preferred embodiments of the camera holder 18, 18'. The third preferred camera holder 18" includes an angled column 18b" with an engagement mechanism 18c" attached to a distal end 19" of the engagement mechanism 18c".

The third preferred camera holder 18" also includes a positioning block 22" at a proximal end of the angled column 18b" and a positioning arm 24" extending from the positioning block 22" and the proximal end of the angled column 18b". The positioning arm 24" preferably has a U-shape including a first positioning arm 24a" and a second positioning arm 24b" that extend generally from a proximal end of the positioning block 22" and the angled column 18b". The positioning arm 24" is preferably configured to retract soft tissue to expose the patient's arches and teeth. The preferred positioning block 22" has an L-shape, a C-shape, a relatively flat shape, a flat shape with a channel or a tray, but is not so limited and may have nearly any size and shape that is able to withstand the normal operating conditions of the positioning block 22" and perform the preferred functions of the positioning block 22", as is described herein. The positioning block 22" and positioning arm 24" are preferably used to orient the camera 12 relative to the patient's teeth while taking images to guide the patient or technician in capturing consistent images by consistently positioning the camera 12 relative to the patient's teeth and arches. The camera axis 12c extends through the U-shape of the positioning arm 24a" in the third preferred embodiment but is not so limited and may be otherwise oriented and configured such that the lens 12b is oriented toward the desired area. The positioning block 22" is preferably comprised of a rigid polymeric or plastic material and the positioning arm 24" is co-molded with the positioning block 22" of the same polymeric or plastic material, but has flexibility, particularly at distal ends of the first and second positioning arms 24a", 24b". The positioning block 22"

preferably has a V-shape that assists with soft tissue retraction, particularly the patient's lips and cheek during image capture. The positioning block 22" is not limited to having the V-shape, the positioning arm 24" is not limited to having the U-shape and the positioning block 22" and arm 24" are not limited to being constructed of the co-molded polymeric or plastic material and may be otherwise designed and configured to withstand the normal operating conditions of the third preferred camera holder 18", perform the preferred functions of the camera holder 18" and otherwise having the general size and configurations of the positioning block 22" and arm 24", as described herein based on the understanding of one having ordinary skill in the art.

Referring to FIGS. 3-3A and 9-14, in operation, the third preferred camera holder 18" is designed and configured for positioning the camera 12, when attached to the engagement mechanism 18c", relative to the patient's arches for capturing buccal images (check, facial or front side) of the patient's teeth. The camera may be comprised of the camera of a smartphone 100 having a housing and a lens 12b for capturing images of the patient's arches and teeth. To capture buccal views of the patient's teeth or arches a retractor, such as a preferred soft tissue retractor 26, is positioned to retract the patient's soft tissue, including lips and cheeks, away from the patient's teeth. The system and method do not require the retractor and may be utilized and performed without the retractor. The preferred soft tissue retractor 26 includes an inner flexible hoop 26a, an outer flexible hoop 26b and a shield 26c extending between the inner and outer flexible hoops 26a, 26b. The preferred retractor 26 has a generally oblong, oval or racetrack-like profile with a void within the inner flexible hoop 26a and the shield 26c generally covering a space between the inner and outer flexible hoops 26a, 26b. Images may be captured through the void with the camera 12 when operating the preferred dental imaging systems 10, 10', 10", 10''', 10'''', 10''''', 10''''''. The inner flexible hoop 26a is preferably designed and configured for positioning at a transition between the patient's gums and lips, while the shield 26c retracts the patient's soft tissue around the mouth under the urging of the outer flexible hoop 26b. The preferred dental imaging system 10 is not limited to utilizing the preferred soft tissue retractor 26 and may utilize nearly any variety and type of retractor that is able to move the patient's soft tissue out of a line of sight of the camera 12 while capturing images of the patient's teeth or arches. The use of the soft tissue retractor 26 or any other alternative retractor is optional and other hardware or methods of moving the patient's soft tissue out of the line of sight of the camera 12 can be used, as long as the camera 12 is able to collect the preferred images of the patient's teeth and arches.

To capture a front buccal view of the patient's teeth or arches, the preferred soft tissue retractor 26 is positioned with the inner flexible hoop 26a adjacent the transition between the patient's gums and lips, thereby causing the shield 26c to urge the lips and soft tissue proximate the patient's mouth away from the teeth and arches. The third preferred camera holder 18" is oriented such that the first or second arm 24a", 24b" of the positioning arm 24" is adjacent the patient's top lip and the other of the first or second arm 24a", 24b" of the positioning arm 24" is adjacent the patient's bottom lip (FIG. 6). The positioning block 22 may be positioned against the buccal side of the patient's teeth for further stability and the camera 12 is oriented toward the patient's front teeth with the third preferred camera holder 18" preferably providing consistency of the image for multiple images taken at multiple different times.

To capture left or right buccal views, the third preferred camera holder 18" is positioned with the positioning arm 24" proximate a buccal side of the patient's molar arches and the positioning block 22" engaging the corner of the patient's lips with a base of its V-shape. The positioning arm 24" and positioning block 22" provide consistency and repeatability of the image by directing the positioning of the camera 12 relative to the patient's teeth for capturing the left and right buccal images.

In the preferred embodiment, the camera holder 18" is rotated one hundred eighty degrees (180°) when switching from right to left or left to right to capture the buccal images. During the image capture of the left and right buccal images, the patient or user may disconnect the camera 12 and rotates the third preferred camera holder 18" one hundred eighty degrees (180°). An alternative method involves rotating the camera view, rather than the camera 12 and lens 12b itself. This rotation of the image can be done via software in the central processor 16.

The third preferred camera holder 18" allows the patient to retract their cheek(s) applying gentle pressure—one cheek at a time—to expose their posterior teeth and provides an improved line of sight for the camera 12 to capture images of the posterior teeth. The third preferred camera holder 18" can be used to collect left or right buccal images by simply rotating the camera holder 18" one hundred eighty degrees (180°). The camera 12 can be disengaged and then reengaged from the third preferred camera holder 18" when switching shots (left or right), or the software of the central processor 16 can automatically flip the orientation of the camera 12 so the camera 12 does not need to be disengaged from the engagement mechanism 18c". The camera holder 18" preferably positions the lens 12b and camera 12 at a preferred and consistent distance and position from the teeth for capturing the images.

The third preferred camera holder 18" could be used in conjunction with a dental imaging device, such as the device described in U.S. Patent Application No. 63/177,982 ("982-APP"); titled, "Dental Imaging Device;" and filed Apr. 22, 2021, as well as International Patent Application No. PCT/US22/25861 ("PCT-861"); titled, "Dental Imaging Device;" and filed Apr. 22, 2022. The preferred camera 12 could clip into the dental imaging device of the 982-APP or PCT-861 and then be disengaged for the occlusal shots or image collection.

By using the camera holder 18" for the buccal shots it also serves as a stabilizer, particularly for the center buccal shots where the positioning arm 24" contacts the patient's face or with the soft tissue retractor 26" with two preferable points of contact (although one point of contact also provides stabilization) and the points of contact are not so limiting.

Lingual Imaging

Figure 4:
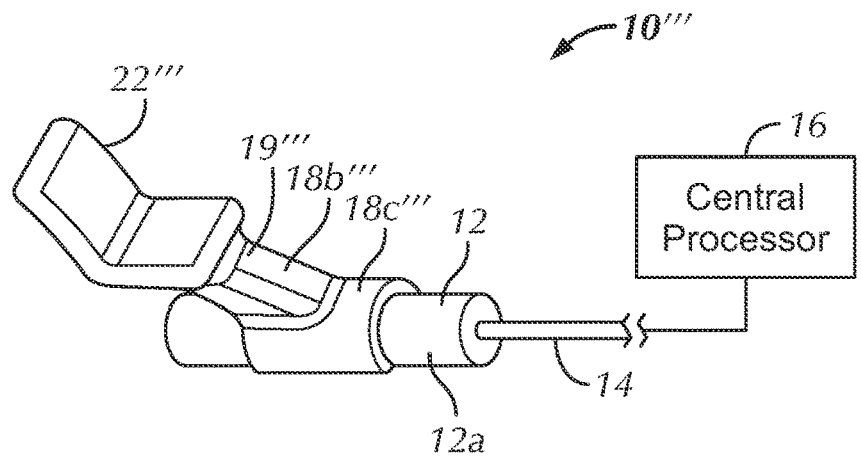
FIG. 4 illustrate a top perspective view of a fourth preferred camera holder and a camera for use with the preferred dental imaging system.
Figure 4A:
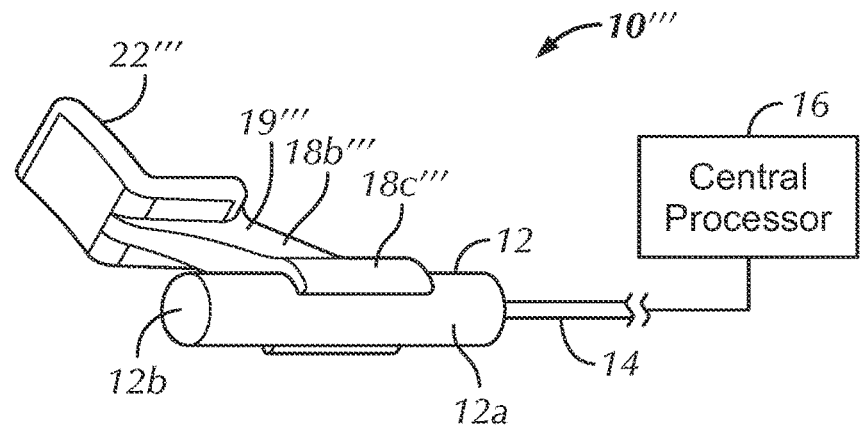
FIG. 4A illustrates bottom perspective view of the camera holder and camera of FIG. 4.
Figure 4B:
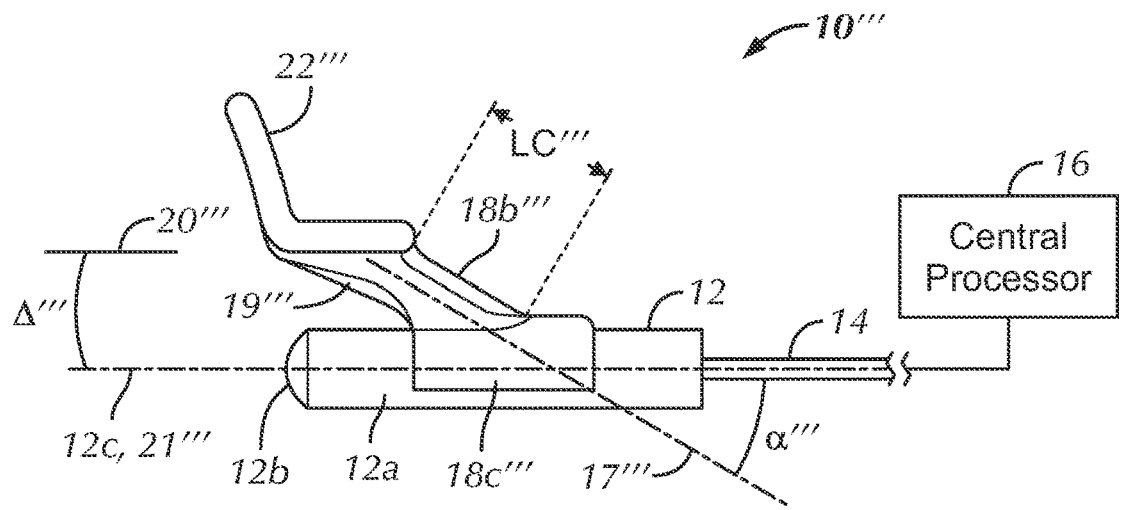
FIG. 4B illustrates a side elevational view of the camera holder and camera of FIG. 4.
Figure 5:
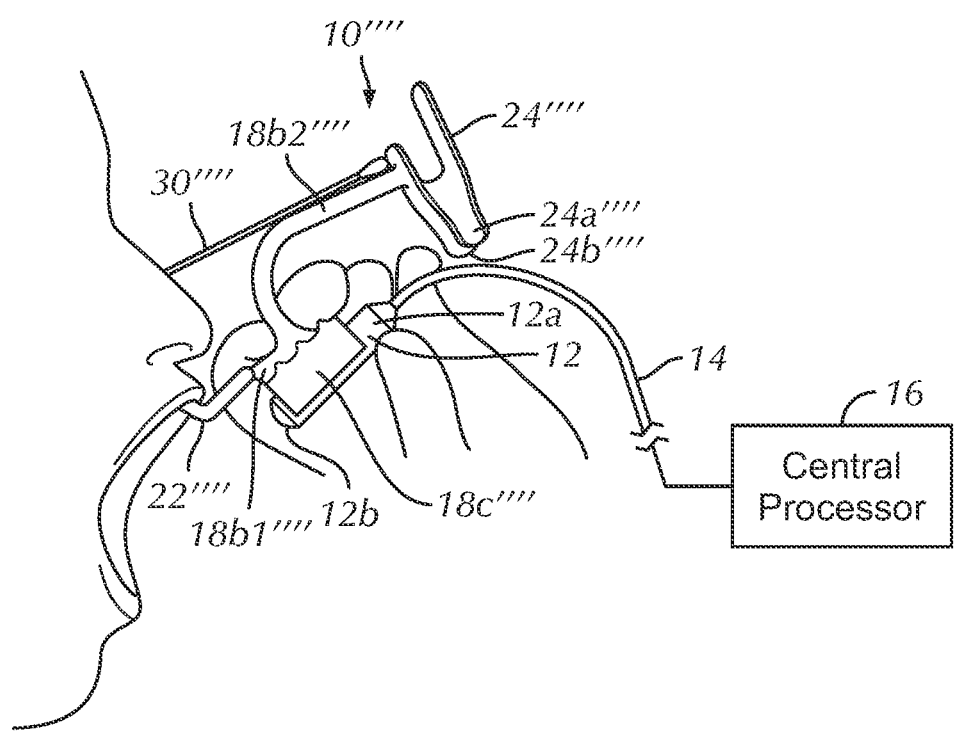
FIG. 5 illustrates a side elevational view of a fifth preferred camera holder and the camera for capturing a lingual image of a patient's arches, wherein the camera and camera holder are oriented to capture a lower lingual image of the patient's arches.

Referring to FIGS. 4-4B, a fourth preferred dental imaging system 10''' includes a camera holder 18''' that holds the camera 12 and orients the camera 12 relative to the patient's mouth to capture the desired images, which are preferably lingual images. The camera holder 18''' of the fourth preferred embodiment is shown in FIGS. 5-5E with the same reference numerals utilized to identify similar or the same features when compared to the first, second and third preferred camera holders 18, 18', 18" and a triple prime symbol ("'") utilized to distinguish the features of the fourth preferred embodiment of the camera holder 18'''' from the features of the first, second and third preferred embodiments of the camera holder 18, 18', 18". The fourth preferred camera holder 18''' includes an angled column 18b''' with an engagement mechanism 18c''' attached to a distal end 19''' of the angled column 18b'''. In the preferred embodiments, the camera holder camera holder 18, 18', 18", 18''' and its components are comprised of an integrally molded polymeric material but are not so limited and may be comprised of separate components secured together constructed of various materials based on designer or operator preferences.

The fourth preferred camera holder 18''' includes a positioning block 22''' at a proximal end of the angled column 18b'''. The positioning block 22''' is preferably used to orient the camera 12 relative to the patient's teeth, preferably a lingual side of the patient's teeth or arches, while taking images to guide the patient or technician in capturing consistent images by consistently positioning the camera 12 relative to the patient's teeth and arches. The positioning block 22''' is preferably comprised of a rigid polymeric or plastic material and the angled column 18b''' and engagement mechanism 18c''' are preferably co-molded with the positioning block 22''' of the same polymeric or plastic material. The positioning block 22" preferably has a V-shape that assists with positioning and orientating the camera 12 relative to the patient's teeth during use and is configured for limited soft tissue retraction during use. The positioning block 22''' is not limited to having the V-shape or to being constructed of the co-molded polymeric or plastic material and may be otherwise designed and configured to withstand the normal operating conditions of the fourth preferred camera holder 18''', perform the preferred functions of the positioning block 22''', have the general size and shape of the positioning block 22''' and otherwise have the configuration of the fourth preferred positioning block 22''', as described herein based on the understanding of one having ordinary skill in the art.

Referring to FIGS. 4-4B and 10-14, in operation, the first, second and fourth preferred camera holders 18, 18', 18''' are designed and configured for positioning the camera 12, when attached to the engagement mechanism 18c, 18c', 18c''', relative to the patient's arches for capturing lingual images (tongue, inner or rear side) of the patient's teeth. To capture lingual views of the patient's teeth or arches the preferred soft tissue retractor 26, although not limiting, is positioned to retract the patient's soft tissue, including lips and cheeks, away from the patient's teeth, as is described herein.

To capture an upper or lower buccal views of the patient's teeth or arches, the preferred soft tissue retractor 26 is positioned with the inner flexible hoop 26a adjacent the transition between the patient's gums and lips, thereby causing the shield 26c to urge the lips and soft tissue proximate the patient's mouth away from the arches. The first, second or fourth preferred camera holder 18, 18', 18''' is oriented such that the tray 18a, 18a' is positioned in alignment with the upper or lower teeth or the positioning block 22''' is engaged proximate the patient's front upper or lower lip or teeth (FIGS. 10-14). The positioning block 22''' of the fourth preferred embodiment may be positioned against the buccal side of the patient's gums or teeth for further stability and the camera 12 is oriented toward the patient's upper or lower teeth, respectively, with the first, second or fourth preferred camera holder 18, 18', 18''' providing consistency of the image for multiple images taken at multiple different times.

Figure 10:
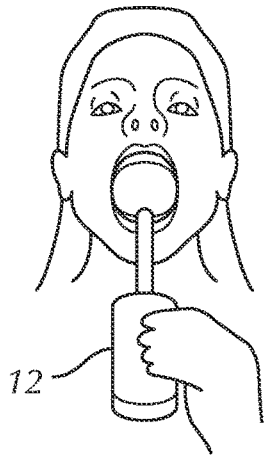
FIG. 10 is a front elevational view of a patient taking an upper occlusal view of the patient's teeth and/or arches using one of the preferred systems.
Figure 11:
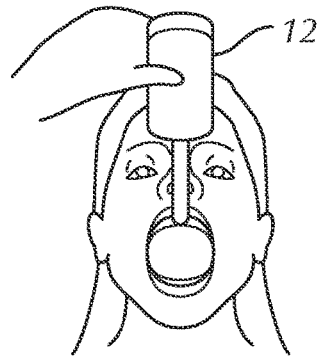
FIG. 11 is a front elevational view of a patient taking a lower occlusal view of the patient's teeth and/or arches using one of the preferred systems.
Figure 12:
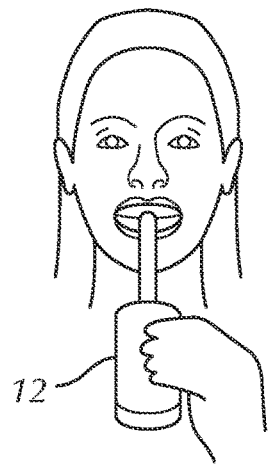
FIG. 12 is a front elevational view of a patient taking an intraoral center view of the patient's teeth and/or arches using one of the preferred systems.
Figure 13:
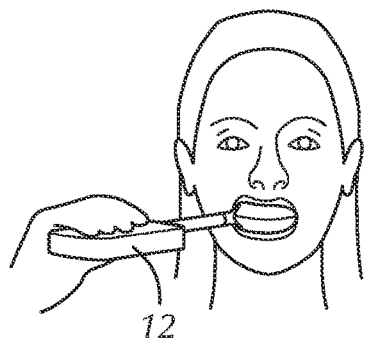
FIG. 13 is a front elevational view of a patient taking a right buccal view of the patient's teeth and/or arches using one of the preferred systems.
Figure 14:
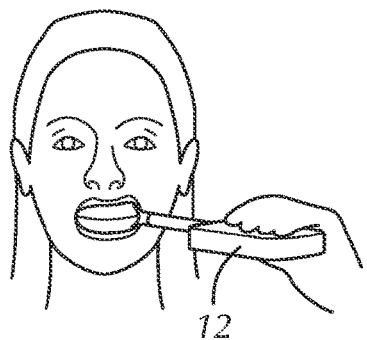
FIG. 14 is a front elevational view of a patient taking a left buccal view of the patient's teeth and/or arches using one of the preferred systems.

For the center buccal shot or collection of central buccal images, the camera holder 18''' can be used to position the lens 12b and camera 12 relative to the center of the patient's mouth. For example, the patient can be told to position the positioning block 22" centered with indentation in the center of the patient's lip (FIGS. 10-12). This may be referred to as the "philtrum."

Combined Camera Holder

Figure 5A:
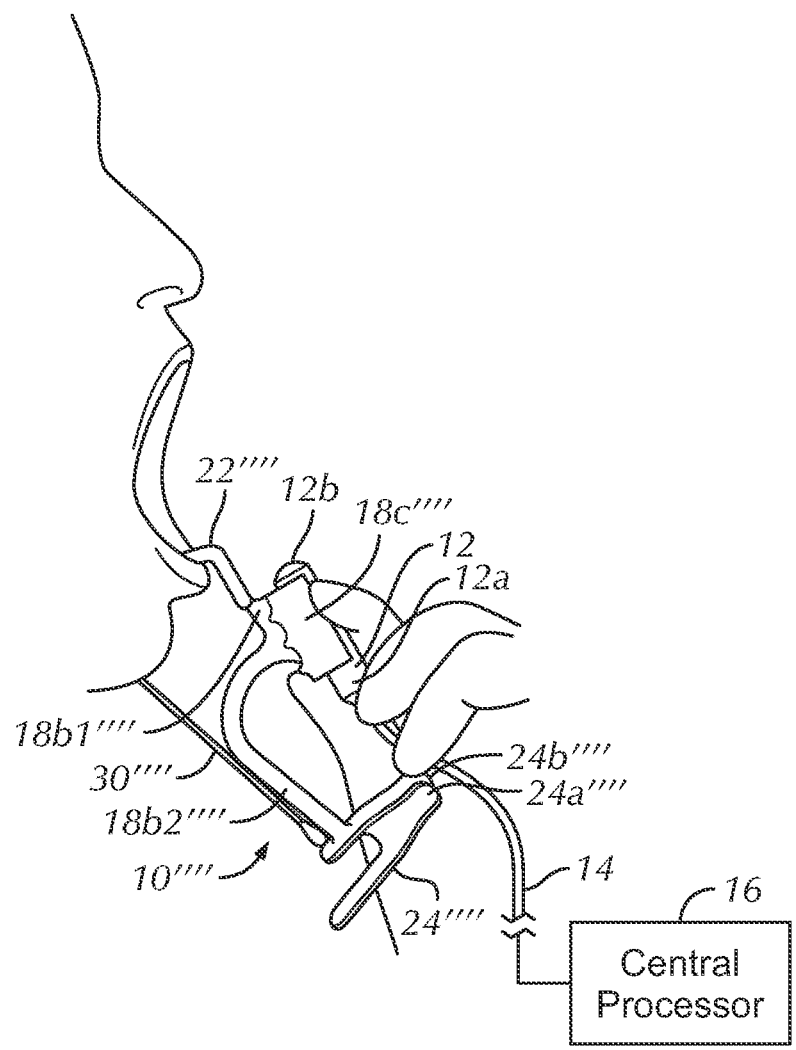
FIG. 5A illustrates a side elevational view of the camera holder and camera of FIG. 5, wherein the camera and cameral holder are oriented to capture an upper lingual image of the patient's arches.

Referring to FIGS. 5 and 5A, a fifth preferred dental imaging system 10'''' includes a camera holder 18'''' that holds the camera 12 and orients the camera 12 relative to the patient's mouth to capture the desired images, which are preferably lingual and buccal images. The camera holder 18'''' in accordance with fifth preferred embodiment is shown in FIGS. 5 and 5A with the same reference numerals utilized to identify similar or the same features when compared to the first, second, third and fourth preferred camera holders 18, 18', 18", 18'''' and a quadruple prime symbol ('''') utilized to distinguish the features of the fifth preferred embodiment of the camera holder 18'''' from the features of the first, second, third and fourth preferred embodiments of the camera holder 18, 18', 18", 18'''. The fifth preferred camera holder 18'''' includes first and second angled columns or arms 18b1'''', 18b2'''' with an engagement mechanism 18c'''' positioned therebetween, the positioning block 22'''' connected to the end of the first angled column or arm 18b1'''' and the positioning arm 24'''' connected to the end of the second angled column or arm 18b2''''. The fifth preferred camera holder 18'''' facilitates collection of lingual and buccal images of the patient's teeth and/or arches, substantially in the same or a similar manner as described above with respect to the third and fourth preferred camera holders 18", 18''', except the camera lens 12b is oriented toward the positioning block 22'''' for acquiring the lingual images and toward the positioning arm 24'''' for acquiring the buccal images. The positioning arm 24'''' also preferably includes an inner wing 24c'''' that may apply force to the lingual side of the patient's cheek to urge the patient's lips and cheeks away from the teeth and molars in particular to enhance capture of buccal images of the rear molars. The inner wing 24c'''' is not limited to being included with the fifth preferred camera holder 18'''' as the camera holder 18'''' my operate without the inner wing 24c''''. In addition, the inner wing 24c'''' may be incorporated with any of the camera holders 18, 18', 18", 18''', 18'''', 18''''' to improve retraction of soft tissue during use or with an alternatively sized, shaped and configured retraction mechanism to assist with soft tissue retraction and exposure of the patient's teeth and arches.

The fifth preferred camera holder 18'''' also may include a spacing arm 30'''' movably attached to the second angled column or arm 18b2'''' that assists the patient with positioning and orienting the camera holder 18'''' and camera 12 relative to the desired area. The spacing arm 30'''' is preferably movable relative to the second angled column or arm 18b2'''' to accommodate various sized and shaped patient anatomies and helps to position/orient the camera 12 relative to the patient's teeth and/or arches. For example, FIG. 5 shows the camera holder 18'''' with a distal end of the spacing arm 30'''' contacting the patient's nose to assist in orienting the camera lens 12b to acquire a lower lingual image, while FIG. 5A shows the camera holder 18'''' with the distal end of the spacing arm 30'''' contacting the patient's chin to assist orienting the camera lens 12b to acquire an upper lingual image. The spacing arm 30'''' is not limited to contacting the nose or chin for orienting the fifth preferred camera holder 18'''' and other portions of the patient's anatomy could be used as well, such as the forehead, check, and other portions of the patient's anatomy. The spacing arm 30'''' is preferably adjustable and/or removable to various positions so that when the spacing arm 30'''' contacts the patient's anatomy, the patient knows that the camera 12 is in the proper position for collecting the desired image. The central processor 16 may send instructions to the patient regarding how to utilize the spacing arm 30'''', whether to use the spacing arm 30'''', where to position the spacing arm 30'''' for collection of particular images, and which desired images to collect. As the shape of each patient's face is different, the spacing arm 30'''' can be "fitted" at a clinical setting, such as a dentist or orthodontist's office, or by the patient themselves, potentially based on instructions from the central processor 16 to determine the appropriate length and placement of the spacing arm 30''''. The length of the spacing arm 30'''' may preferably be designed and configured to have different lengths for different patient anatomy or may be adjustable relative to the second angled column or arm 18b2''''.

Figure 9:
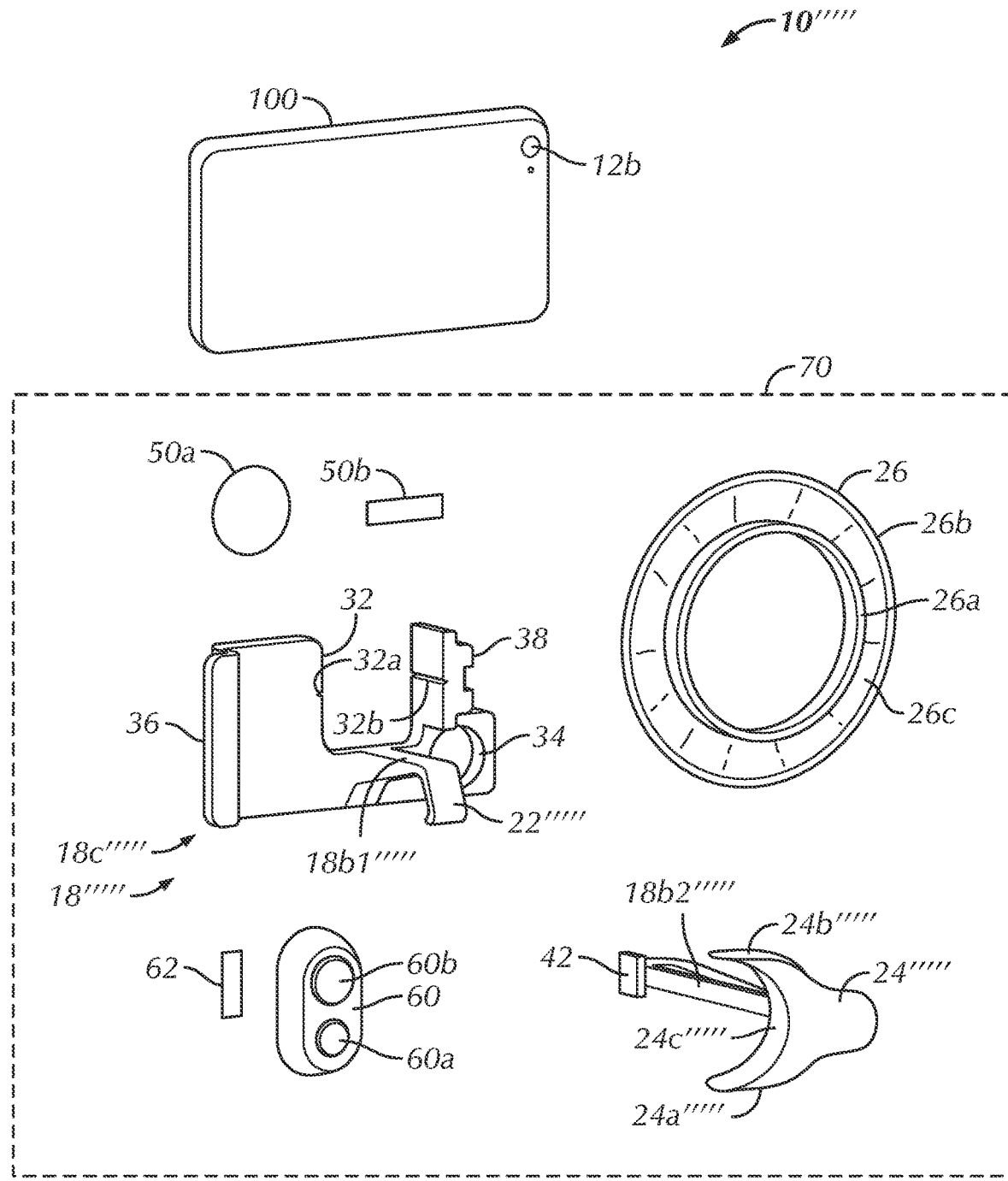
FIG. 9 is a front perspective, exploded view of a preferred camera system in accordance with a sixth preferred embodiment of the present invention.

Referring to FIG. 9, a sixth preferred dental imaging system 10''''' includes a camera holder 18''''' that holds the camera 12, which is preferably incorporated into a smartphone 100 and the housing of the smartphone 100 and orients the camera lens 12b of the camera 12 relative to the patient's mouth to capture the desired images, which are preferably lingual and buccal images. The camera holder 18''''' in accordance with sixth preferred embodiment is shown in FIG. 9 with the same reference numerals utilized to identify similar or the same features when compared to the first, second, third, fourth and fifth preferred camera holders 18, 18', 18'', 18''', 18'''' and a quintuple prime symbol (''''') utilized to distinguish the features of the sixth preferred embodiment of the camera holder 18''''' from the features of the first, second, third, fourth and fifth preferred embodiments of the camera holder 18, 18', 18'', 18''', 18''''. The sixth preferred camera holder 18''''' includes an engagement mechanism 18c''''' with the first angled arm 18b1''''' and positioning block 22''''' extending therefrom, adhesive strips 50a, 50b, and the second angled arm 18b2''''' and positioning arm 24''''' that may be co-molded but separate from the engagement mechanism 18c'''''. The sixth preferred engagement mechanism 18c''''' and the adhesive strips 50a, 50b are utilized to connect the smartphone at least temporarily 100 to the dental imaging system 10'''''. The engagement mechanism 18c''''' may include a U-shaped opening 32, a finger grip hole 34, a handle 36 and a connection slot 38. A proximal end of the second angled arm 18b2''''' includes a connection hub 42 that is removably mountable to the connection slot 38 to releasably connect the second angled arm 18b2''''' and the positioning arm 24''''' to the engagement mechanism 18c'''''. The sixth preferred dental imaging system 10''''' also may include the soft tissue retractor 26 and a remote capture button 60 with a trigger adhesive strip 62. The remote capture button 60 of the preferred embodiment includes a power button 60a and a trigger button 60b.

The sixth preferred dental imaging system 10''''' may be delivered to a patient, user, clinician, or other individual as a kit, potentially in a package 70, such as a box, bag, or other packaging, except for the smartphone 100, which is preferably comprised of the patient's or other user's smartphone 100. The sixth preferred dental imaging system 10''''' is not limited to utilizing the user's smartphone 100 and the associated camera 12 with the lens 12b''''' and may use the dedicated cameras 12 shown and described herein or other cameras or equipment that permit collection of the images of the patient's arches and teeth. The sixth preferred dental imaging system 10''''', however, preferably utilizes the user's smartphone 100, particularly because the sixth preferred camera holder 18''''' and engagement mechanism 18c''''' are designed and configured for use with the user's smartphone 100.

The camera 12 of the sixth preferred embodiment is incorporated into the smartphone 100 having a housing and a lens 12b. The first angled arm or column 18b1''''' extends from the generally planar plate or portion of the engagement mechanism 18c''''' with the positioning block 22''''' connected to a proximal end of the first angled arm or column 18b1'''''. The engagement mechanism 18c''''' is positioned at a distal end of the first angled arm or column 18b1'''''. The engagement mechanism 18c''''' is configured for releasably mounting the smartphone 100 and associated camera 12 with the camera lens 12b oriented toward the distal end of the first angled arm or column 18b1''''' in a mounted configuration. The positioning block 22''''' is configured to contact the patient's arches, teeth, cheeks or lips when collecting images with the camera. The camera holder 18''''' orients the camera lens 12b relative to the patient's arches and teeth such that the desired images may be collected. The camera of the smartphone 100 has a camera axis that extends or projects generally perpendicularly relative to the planar or flat portion of the engagement mechanism 18c''''' to direct the field of view of the camera toward the positioning block 22'''''.

The sixth preferred dental imaging system 10''''' is preferably supplied to the patient in the package 70 as the kit and the component parts are removed from the package 70. The user or patient's smartphone 100 is preferably attached to the engagement mechanism 18c''''' with the adhesive strips 50a, 50b such that the lens 12b is centered between positioning indicators 32a, 32b adjacent edges of the U-shaped opening 32. The lens 12b is not limited to being centered between the positioning indicators 32a, 32b and the lens 12b may be otherwise positioned relative to the engagement mechanism 18c''''' such that the lens 12b is consistently positioned relative to the engagement mechanism 18c''''' during each use of the dental imaging system 10'''''. The remote capture button 60 is preferably secured to the engagement mechanism 18c''''' between the U-shaped opening 32 and the handle 36 but is not so limited and may be integrally formed with the engagement mechanism 18c''''', otherwise positioned relative to the engagement mechanism 18c''''' or maintained separately from the engagement mechanism 18c'''''. The second angled arm 18b2''''' and positioning arm 24''''' may be selectively mounted and removed from the engagement mechanism 18c''''' by engaging or disengaging the connection slot 38 and the connection hub 42. The sixth preferred dental imaging system 10''''' may collect images of the patient's teeth and arches utilizing a similar method to that described above with respect to the fifth preferred dental imaging system 10''''.

In operation, the patient preferably receives the kit with the components of the sixth preferred dental imaging system 10''''' in the package 70. The components are removed from the package 70 and the engagement mechanism 18c''''' is connected to the patient's smartphone 100 utilizing the adhesive strips 50a, 50b such that the lens 12b is centered between the positioning indicators 32a, 32b. The remote capture button 60 is connected to the opposite side of the engagement mechanism 18c''''' utilizing the trigger adhesive strip 62. The patient is then able to manipulate the assembled or connected smartphone 100 and engagement mechanism 18c''''', potentially by grasping the finger grip hole 34 and/or the handle 36. With the soft tissue retractor 26 retracting the patients lips and the lens 12b facing the users teeth and arches, the patient may stand in front of a mirror (not shown) with a display (not shown) of the smartphone 100 visible in the mirror. The patient is, thereby, able to view the image that will be collected from the reflection of the display of the smartphone 100 and depresses the trigger button 60b when the image is considered acceptable or the smartphone 100 or central processor indicates to the patient that the image is acceptable. The patient may collect the images alone without assistance from another individual or a medical professional or clinician such that the images may be collected by the patient without visiting a medical professional's office. The images are preferably collected with the flash of the smartphone 100 activated to illuminate the target area. Upper arch, lower arch, and center arch images (FIGS. 10-12) may be collected utilizing the engagement mechanism 18c'''''' without the second angled arm 18b2'''''' attached to the engagement mechanism 18c''''''. Left and right buccal images (FIGS. 13 and 14) may be collected utilizing the engagement mechanism 18c'''''' with the second angled arm 18b2'''''' and the positioning arm 24'''''' attached thereto. Following collection of the images, the smartphone 100 may be disconnected from the engagement mechanism 18c'''''', the components may be cleaned and/or sterilized, and the components may be positioned back into the package 70 for subsequent use.

Figure 16:
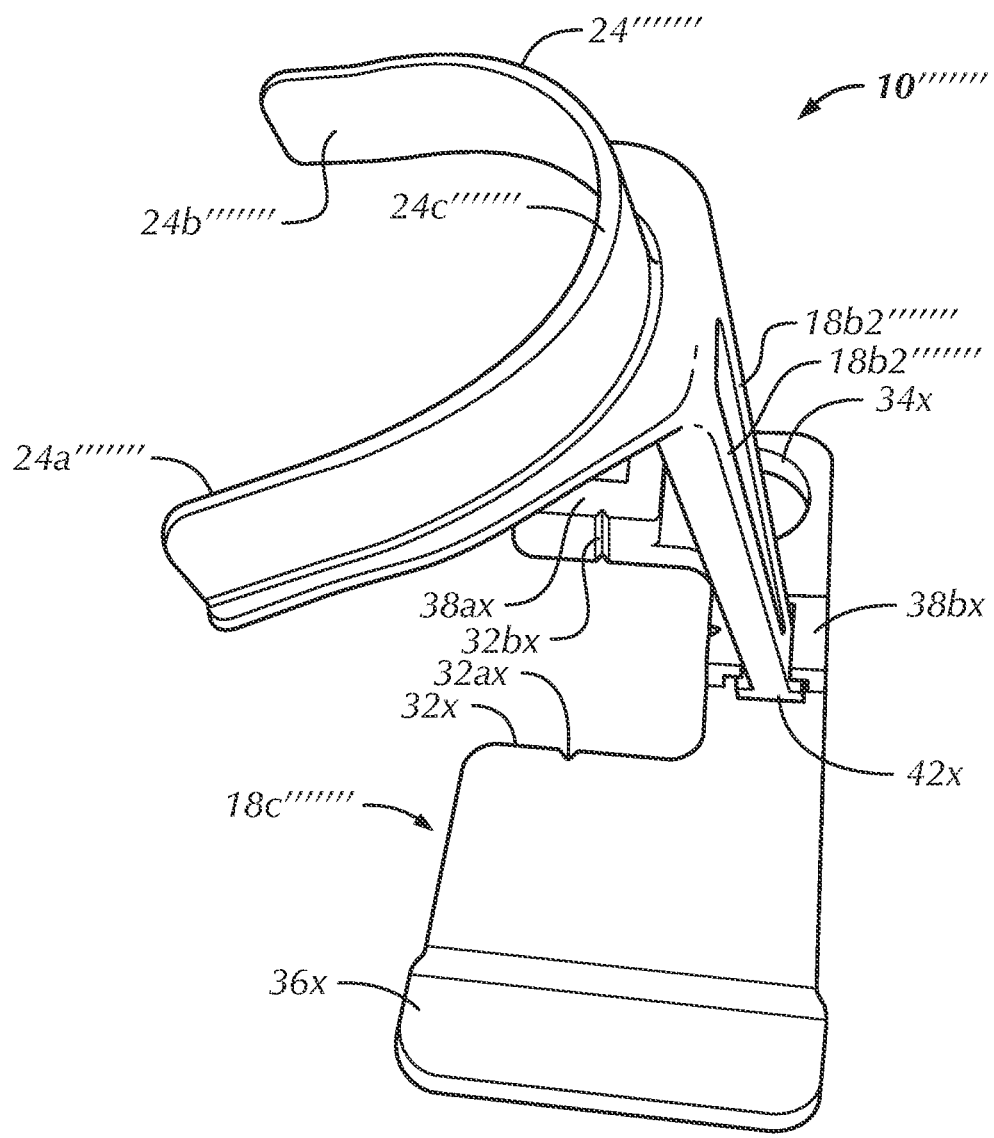
FIG. 16 is a front perspective view of a preferred camera system in accordance with an eighth preferred embodiment of the present invention.
Figure 17:
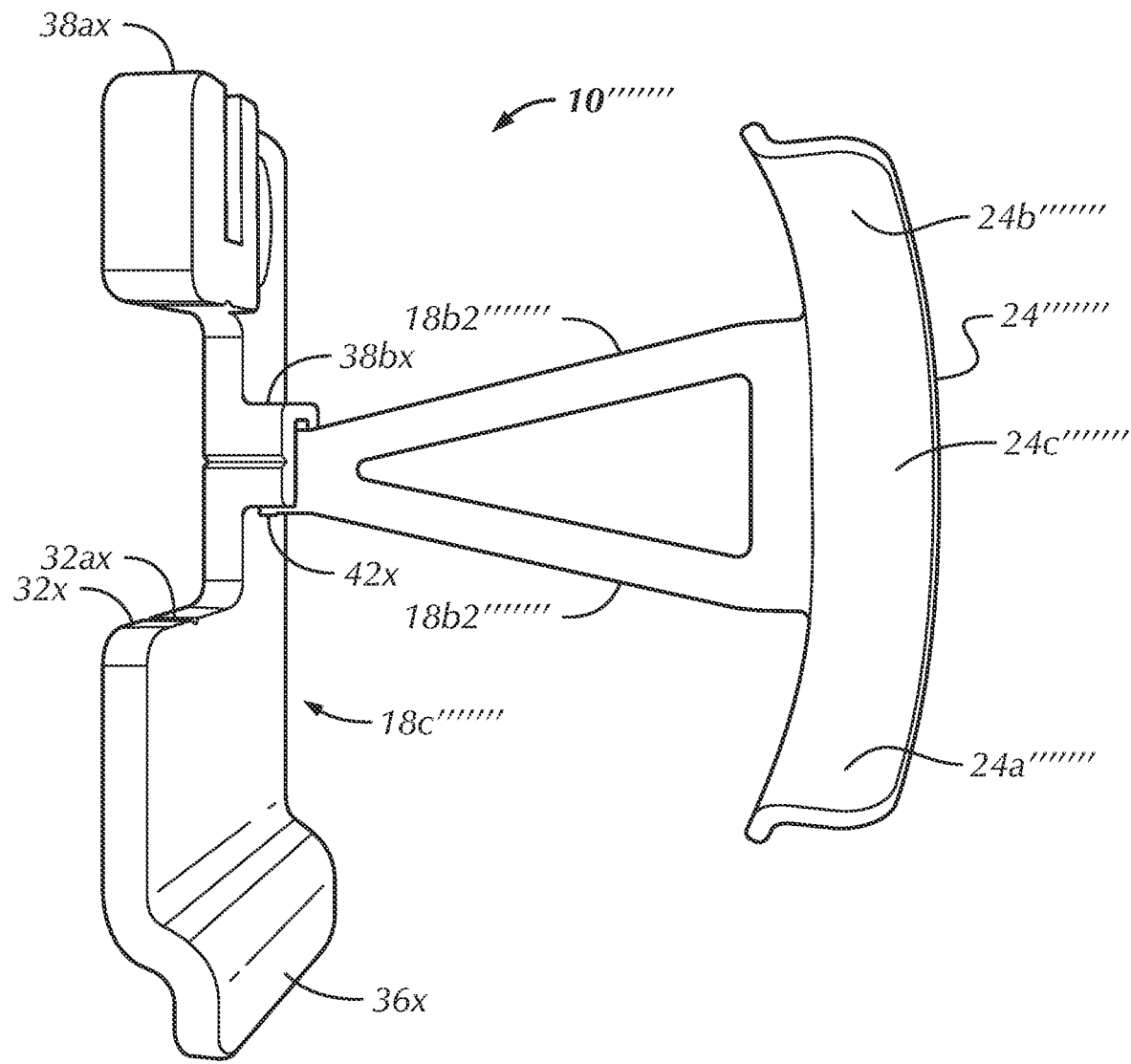
FIG. 17 is a side elevational view of the camera system of FIG. 16.
Figure 18:
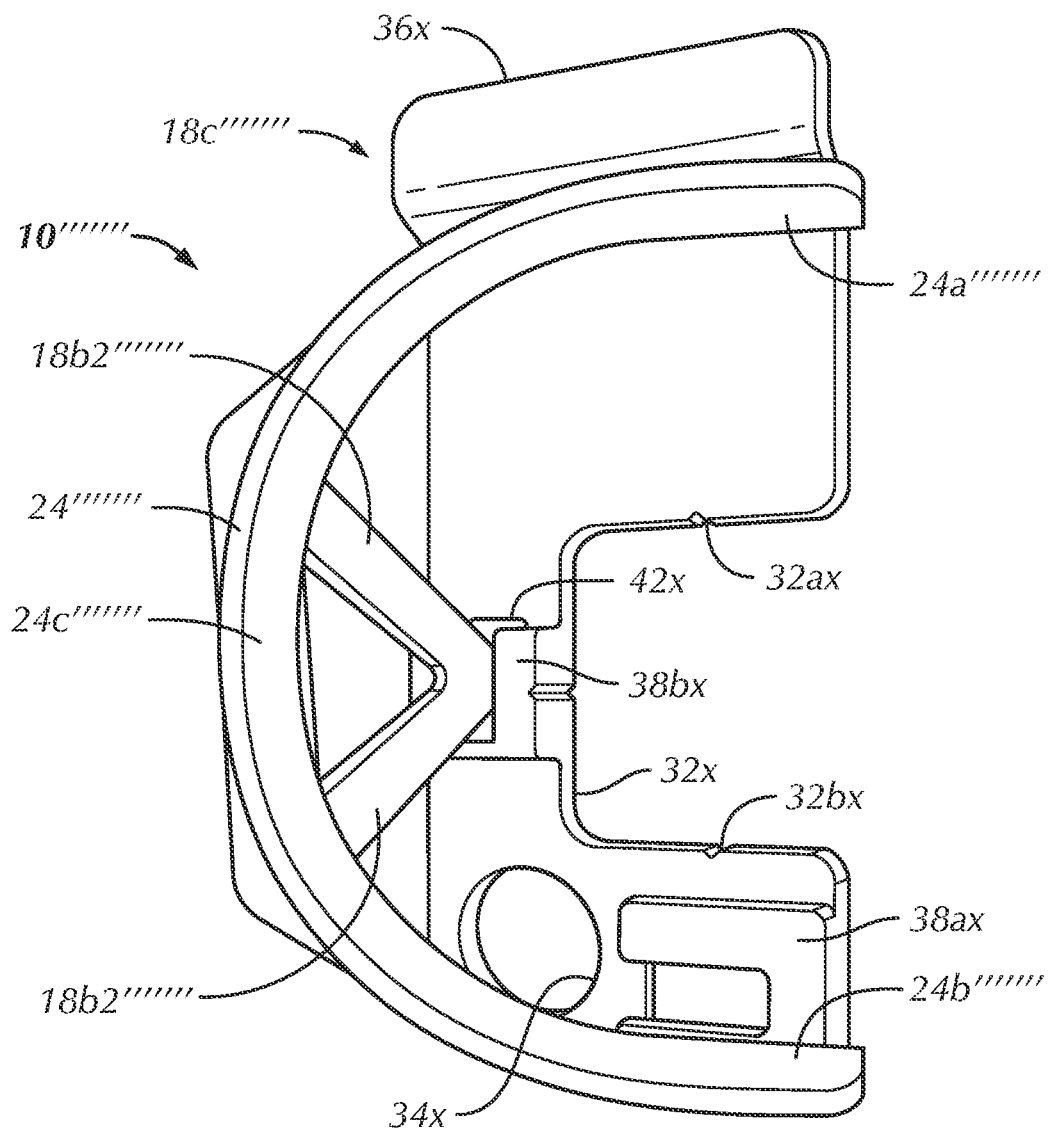
FIG. 18 is a front elevational view of the camera system of FIG. 16.
Figure 19:
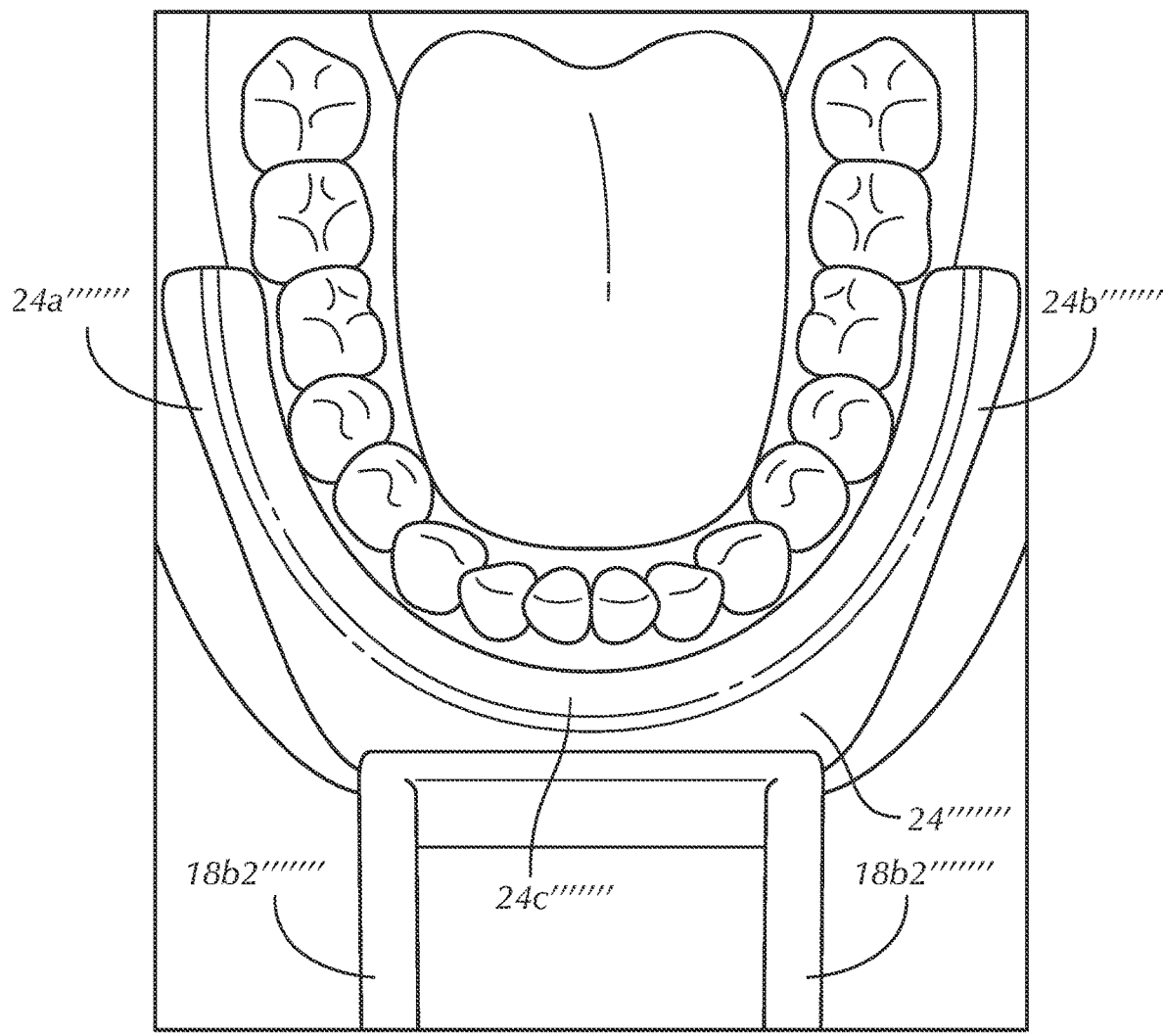
FIG. 19 is a lower occlusal view of a patient's lower arch with a positioning arm of the camera system of FIG. 16 positioned against the patient's lower arch.
Figure 20:
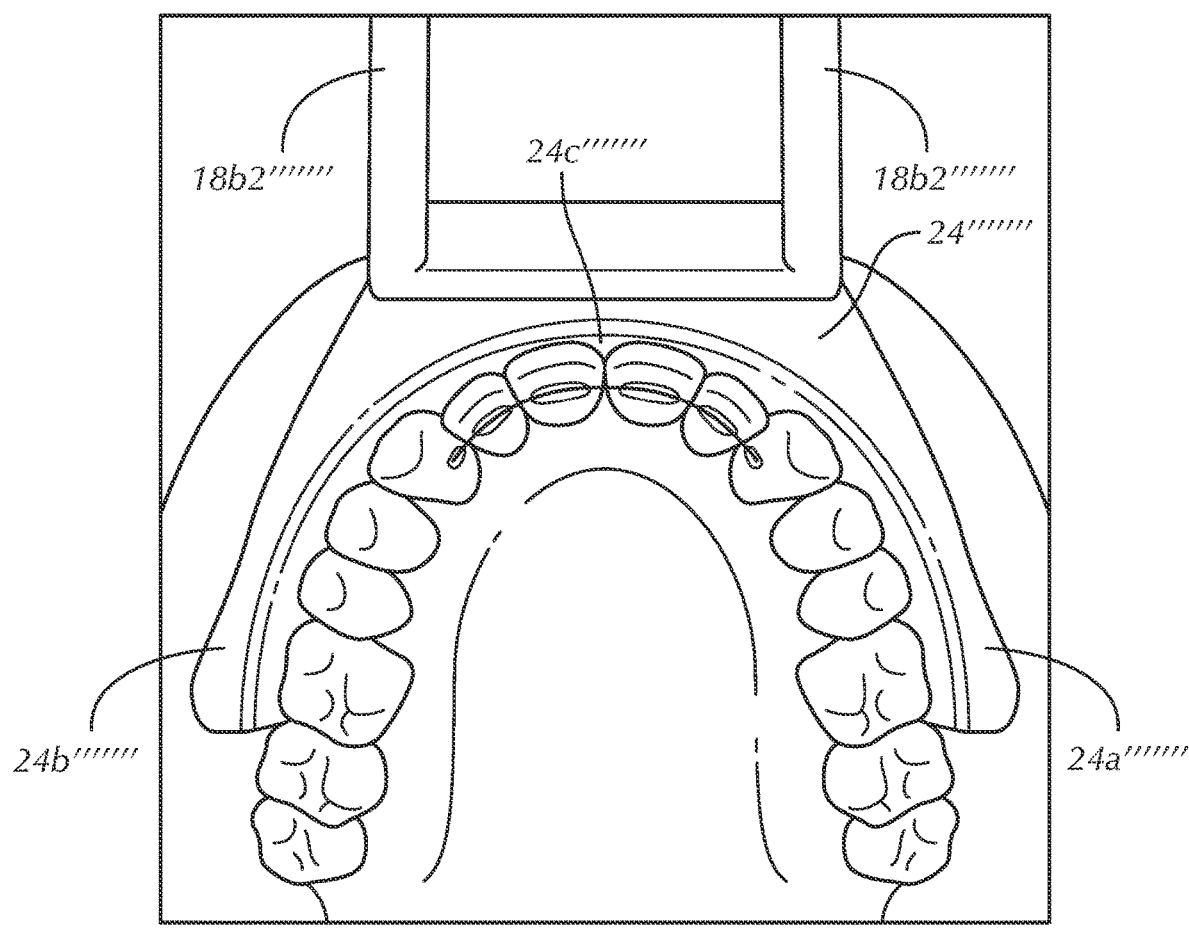
FIG. 20 is an upper occlusal view of a patient's upper arch with a positioning arm of the camera system of FIG. 16 positioned against the patient's upper arch.

Referring to FIGS. 16-20, an eighth preferred dental imaging system 10'''''' includes a camera holder 18'''''' that holds the camera 12, which is preferably incorporated into a smartphone 100 and the housing of the smartphone 100 and orients the camera lens 12b of the camera 12 relative to the patient's mouth to capture the desired images, which are preferably upper and lower occlusal images. The lens 12b is preferably centered between the positioning indicators 32a, 32b in the mounted configuration. The camera holder 18'''''' in accordance with eighth preferred embodiment is shown in FIGS. 16-18 with the same reference numerals utilized to identify similar or the same features when compared to the first, second, third, fourth, fifth, sixth and seventh preferred camera holders 18, 18', 18'', 18''', 18'''', 18''''', 18'''''' and a septule prime symbol (''''''') utilized to distinguish the features of the eighth preferred embodiment of the camera holder 18'''''' from the features of the first, second, third, fourth, fifth, sixth and seventh preferred embodiments of the camera holder 18, 18', 18'', 18''', 18'''', 18''''', 18''''''. The eighth preferred camera holder 18'''''' has similar features and operation relative to the sixth preferred camera holder 18'''' with a modified positioning arm 24'''''' for positioning and orienting the lens 12b toward the patient's arches and retraction of soft tissue proximate the patient's teeth to improve visibility of the teeth and gums for capturing the images. The eighth preferred engagement mechanism 18c'''''' does not include the co-molded first angled arm or column 18b1'''' but may include a separate first angled arm or column that is releasably engageable with first and/or second connection slots 38ax, 38bx.

The eighth preferred engagement mechanism 18c'''''' has similar or the same features when compared to the sixth preferred engagement mechanism 18c'''' and an "x" suffix is utilized to distinguish the features of the eighth preferred engagement mechanism 18c'''''' from the features of the sixth preferred engagement mechanism 18c'''' that do not utilize the prime symbols. The eighth preferred engagement mechanism 18c'''''' includes the U-shaped window 32x, the finger grip hole 34x, the handle 36x and the second angled arm 18b2'''''' connected to the positioning arm 24''''''. The second angled arm 18b2'''''' includes the connection hub 42x at a proximal end that is preferably, removably mountable to the engagement mechanism 18c'''''' at the first or second connection slots 38ax, 38bx. The first and second connection slots 38ax, 38bx have a similar function compared to the connection slot 38. The first and second connection slots 38ax, 38bx are configured to slidably receive the connection hub 42x therein by sliding the connection hub 42x into the first or second connection slots 38ax, 38bx generally laterally or parallel to a surface of the engagement mechanism 18c''''''.

Figure 21:
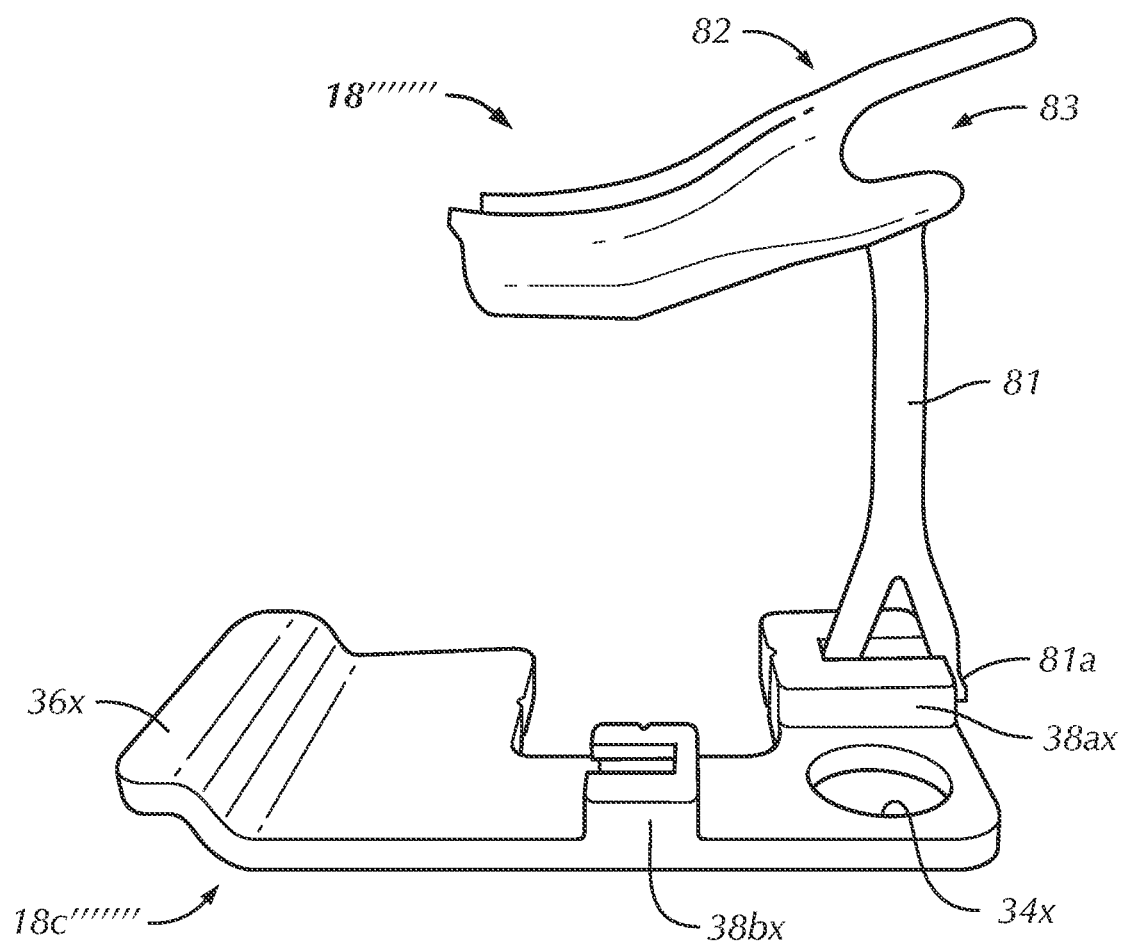
FIG. 21 is a side perspective view of the camera system of FIG. 16.

Referring to FIG. 21, the eighth preferred camera holder 18'''''' may also include a buccal attachment 80 that is removably mountable to the first connection slot 38ax for collecting buccal images of the patient's teeth and arches. The buccal attachment 80 includes an angled arm 81 with a connection hub 81a at one end and a positioner 82 at an opposite end of the angled arm 81. The positioner 82 is comprised of a generally U-shaped structure with an external groove 83 that accepts and retracts the patient's cheecks at the sides of the patient's mouth in an operating position to retract the patient's cheeks away from the patient's teeth so that a buccal view of the patient's teeth may be acquired during use. This configuration of the external groove 83 and the angled arm 81 that are removably connected to the first connection slot 38ax are designed and configured for orienting the camera toward the patient's teeth and retracting the patient's teeth so that the buccal images of the patient's teeth and gums may be acquired (See FIGS. 13 and 14).

Connectivity

Referring to FIGS. 1-14, the camera 12 or other imaging device can be connected by the power and data cord 14 or an alternative cord to a smartphone 100, computer tablet, mobile device, or personal computer, which comprises the central processor 16, or may be connected by wireless means such as Bluetooth or Wi-Fi to the central processor 16. In the preferred embodiments the user may look at the screen of the central processor 16, such as a screen on a smartphone or tablet 100, to preview the image before capturing the image or images. The screen, smartphone interface or App may include prompts driven by the central processor 16 to guide the user while they capture the images. By following either audio, visual or written prompts, the user may be instructed as to what images are to be taken in a specific sequence as well as any specific instructions they should follow to correctly capture the desired images using the dental imaging system 10, 10', 10'', 10''', 10'''', 10''''', 10'''''', 10'''''''. As an example, the prompt may request that the user place the camera holder 18, 18', 18'', 18''', 18'''', 18''''', 18'''''', 18''''''' into the proper position, adjust the soft tissue retractor 26 or open their mouth wider. When done correctly the user will be notified that the images are acceptable based on a signal from the central processor 16 that may be represented by an audible sound or a visual cue on a smartphone 100, the screen, or other notification mechanism of the central processor 16.

Positioning Devices

The camera lens 12b and camera 12 can be used in conjunction with one or more positioning devices to properly position the lens 12b for optimal images. The positioning devices are preferably comprised of the camera holder 18, 18', 18'', 18''', 18'''', 18''''', 18'''''', 18''''''' and may include many alternative shapes and sizes, as long as the camera holder 18, 18', 18'', 18''', 18'''', 18''''', 18'''''', 18''''''' is able to hold and orient the camera 12, position the camera 12 for taking images, withstand the normal operating conditions of the camera holder 18, 18', 18'', 18''', 18'''', 18''''', 18'''''', 18''''''', and perform the preferred function of the camera holder 18, 18', 18'', 18''', 18'''', 18''''', 18'''''', 18'''''''. The camera holder 18, 18' of the first and second preferred embodiments includes the tray 18a, 18a' in the shape of a dental arch with the built-in engagement mechanism 18c, 18c'. The first and second camera holders 18, 18' include the angled column 18*b*, 18*b*' and the engagement mechanism 18*c*, 18*c*'. The tray 18*a*, 18*a*' may be comprised of a full arch or partial arch tray 18*a*, 18*a*'. The tray 18*a*, 18*a*' can be sized to a specific patient based on one of: a sizing assessment method (small, medium, large, etc.) or may be custom shaped and sized to an individual patients' arches.

The tray 18*a*, 18*a*' can have a means of temporarily securing the tray 18*a*, 18*a*' to the patient's teeth and/or gums so that the lens 12*b* is positioned in the ideal position and so that the image is stable. Such means may include: a) suction cups fabricated into the tray 18*a*, 18*a*' which contact the occlusal surface of the patient's teeth, b) applying torsion from the sides of the tray 18*a*, 18*a*' against the patient's gums and/or teeth, c) forming inner surfaces of the tray 18*a*, 18*a*' to the patient's mouth or d) any other method of temporarily securing the tray 18*a*, 18*a*' relative to the patient's arches while the images are being captured. The tray 18*a*, 18*a*' is preferably sized to be used with a specific arch (maxillary or mandibular or may be sized to be used with either arch). The trays 18*a*, 18*a*' are not limited to comprising generally full mouth trays 18*a*, 18*a*', as shown in FIGS. 1-2A, and may be configured as relatively small trays 18*a*, 18*a*', so as just to engage one of the front teeth of the patient, several teeth or nearly any portion of the patient's teeth or gums to provide a support for the camera holders 18, 18' as would be understood by one having ordinary skill in the art based on the present disclosure.

The engagement mechanism 18*c*, 18*c*', 18*c*'', 18*c*''', 18*c*'''', 18*c*''''', 18*c*'''''', 18*c*''''''' enables the camera 12 to snap into it, connect via the adhesive strips 50*a*, 50*b* or it may connect via other means, such as by fastening, clamping, hook and loop material, bonding or other securing systems or techniques. The engagement mechanism 18*c*, 18*c*', 18*c*'', 18*c*''', 18*c*'''', 18*c*''''', 18*c*'''''', 18*c*''''''' can be in a fixed position relative to the angled column 18*b*, 18*b*', 18*b*'', 18*b*''', 18*b*1'''', 18*b*2'''', 18*b*1''''', 18*b*2''''', 18*b*'''''', 18*b*1''''''', 18*b*2''''''' or adjustable by the user. The engagement mechanism 18*c*, 18*c*', 18*c*'', 18*c*''', 18*c*'''', 18*c*''''', 18*c*'''''', 18*c*''''''' is preferably designed to position the camera lens 12*b* and the camera 12 or smartphone 100 in an optimal position for taking desired images, as determined by the designer, dentist, orthodontist or manufacturer. The engagement mechanism 18*c*, 18*c*', 18*c*'', 18*c*''', 18*c*'''', 18*c*''''', 18*c*'''''', 18*c*''''''' may have a retraction feature to adjust the positioning of the camera 12 and lens 12*b* and may enable the camera 12 to snap into the engagement mechanism 18*c*, 18*c*', 18*c*'', 18*c*''', 18*c*'''', 18*c*''''', 18*c*'''''', 18*c*''''''' or it may connect via another means. The preferred engagement mechanism 18*c*, 18*c*', 18*c*'', 18*c*''', 18*c*'''' of the first, second, third, fourth and fifth preferred embodiments has a semi-circle shape on one or more sides that can be placed partially inside the lips and conforms to at least a portion of the housing 12*a* to engage the housing 12*a* but is not so limited and may have nearly any size and shape that is able to engage and secure the camera 12 to the angled column or arm 18*b*, 18*b*', 18*b*'', 18*b*''', 18*b*1'''', 18*b*2'''', 18*b*1''''', 18*b*2''''', 18*b*'''''', 18*b*1''''''', 18*b*2''''''', 18*b*1''''''', 18*b*2'''''''. The preferred semi-circular shape of the engagement mechanism 18*c*, 18*c*', 18*c*'', 18*c*''', 18*c*'''' enables the patient to snap lock the camera 12 to the camera holder 18, 18', 18'', 18''', 18'''', but is not so limited and may otherwise engage the camera 12.

The camera holder 18, 18', 18'', 18''', 18'''', 18''''', 18'''''', 18''''''' of the preferred embodiments may include features or elements that provide points of contact with the patient's face. These points of contact may be utilized by the user to appropriately position the camera holder 18, 18', 18'', 18''', 18'''', 18''''', 18'''''', 18''''''' and camera 12 to optimize and normalize the images that are taken of the patient's teeth and arches, such as the trays 18*a*, 18*a*', the positioning arm 24'' and the positioning blocks 22'', 22'''. The camera holder 18, 18', 18'', 18''', 18'''', 18''''', 18'''''' preferably holds the camera 12 and in alternative preferred embodiments contacts one or more points on the front of the patient's face, the soft tissue retractor 26, the patient's teeth or other reference areas, zones or points (as opposed to the lips) to provide stability and a relatively standard focal distance while capturing the images of the patient's arches and teeth.

Referring to FIGS. 10-14, the patient may be directed by the central processor 16 to acquire images of their teeth and/or arches for analysis and manipulation, such as for creating a three-dimensional ("3D") model of the patient's teeth and arches, determining teeth and gum health, analyzing teeth movement based on a treatment plan, and other analysis and evaluation purposes. As non-limiting examples, the central processor 16 may direct the patient to collect upper occlusal, lower occlusal, intraoral center, right buccal, left buccal and other views of desired areas of the patient's teeth and/or arches. The upper occlusal, lower occlusal, intraoral center, right buccal and left buccal views may each be taken using the fifth and sixth preferred camera holders 18'''', 18''''', while the upper occlusal and lower occlusal views may also be acquired using the first, second and fourth preferred camera holders 18, 18', 18''' and the right buccal and left buccal views may further be acquired using the third preferred camera holder 18''. The central processor 16 may direct the patient to collect these images, such as by messaging, for example, by sending the images of FIGS. 10-14 to the patient and requesting acquisition of the desired images. The example images are not limiting and the central processor 16 may request more or less images from the patient, depending on the treatment plan, clinical situation or other factors. As shown in FIGS. 10-14, the patient may acquire the images utilizing a single hand to manipulate the camera 12 and the camera holder 18, 18', 18'', 18''', 18'''', 18''''' into an orientation to acquire the desired images and depress the capture button 12*d* to acquire the desired image. The desired images are preferably transmitted to the central processor 16 wirelessly, which may be a smartphone 100 or central server that further analyzes or manipulates the collected images.

Optional Cheek Retractors

Referring to FIG. 9, the dental imaging systems 10, 10', 10'', 10''', 10'''', 10''''', 10'''''', 10''''''' may be used in conjunction with and include a variety of cheek retraction systems and methods to create space between the teeth and the cheeks, which otherwise may block the view of one or more teeth while capturing the images. Such methods include but are not limited to full mouth retractors such as a Nola Retractor, photo check retractors, cotton or other flexible material placed between the check and gums, Optragate brand style flexible cheek retractors/soft tissue retractor 26 or other systems or methods that are able to retract the patient's teeth out of the field of view of the camera 12 during image capture to improve and normalize the images. The dental imaging systems 10, 10', 10'', 10''', 10'''', 10''''', 10'''''', 10''''''' of the preferred embodiments may, particularly utilize the soft tissue retractor 26 to retract the patient's soft tissue proximate the lips to provide a generally unobstructed or enhanced line of sight to the patient's teeth and arches.

Optional Chin Rest

The dental imaging system 10 may also be used with a chin rest (not shown). The chin rest could have attachments to optimally position the camera 12 relative to patient's dental arches.

Electronic Image Correction and Formatting

Referring to FIGS. 1-14, the dental imaging systems 10, 10', 10", 10''', 10'''', 10''''', 10'''''', 10''''''' may include the central processor 16, which may be comprised of a smartphone 100, computer tablet or personal computer. The central processor 16 may have image correction and formatting software to ensure that the captured images are of sufficient quality, cropped consistently, sized consistently and that they are stored according to image type. The image correction and formatting software is not limiting and the dental imaging system 10, 10', 10", 10''', 10'''', 10''''', 10'''''', 10''''''' may be operated without the image correction and formatting software without significantly impacting the desired operation and function of the dental imaging system 10, 10', 10", 10''', 10'''', 10''''', 10''''''.

The dental imaging systems 10, 10', 10", 10''', 10'''', 10''''', 10'''''', 10''''''' may take images that have much higher resolution focused on a relatively narrow area of the patient's teeth or arches. In an alternative preferred embodiment, the camera 12 may include an optional auxiliary lens that can be placed over the standard lens 12b that acts as a magnifier. The central processor 16 may alternatively direct the camera 12 to have different magnification options or interchangeable lenses to capture narrower or clearer images. In the preferred embodiments, the buccal images are preferably processed so that the images orient the arches in a perpendicular manner (so that there is consistency to the view displayed). The central processor 16 of the dental imaging system 10, 10', 10", 10''', 10'''', 10''''', 10'''''', 10''''''' may be capable of modifying/adjusting the angle of the dental arches so that the view appears to have been taken from a ninety degree (90°) angle relative to the dental arch. The preferred central processor 16 is also may be designed and configured to identify and determine the orientation of the camera lens 12b relative to any of the camera holders 18, 18', 18", 18''', 18'''', 18''''', 18'''''', 18'''''''. This could include a printed mark or indentation on either or both the camera 12 and camera holder 18, 18', 18", 18''', 18'''', 18''''', 18'''''', 18''''''' or references know by the central processor 16 that allows determination of the orientation of the camera 12 relative to the camera holders 18, 18', 18", 18''', 18'''', 18''''', 18'''''', 18''''''' or to the patient.

Image Splicing and Adjusting for Distortions

The preferred dental imaging system 10, 10', 10", 10''', 10'''', 10''''', 10'''''', 10''''''' may include multiple cameras 12 with camera lenses 12b to capture the images. In a preferred case where more than one camera lens 12b is used, the software of the central processor 16 may include a feature capable of splicing multiple images together to provide an enhanced view of the patient's arches. The software may automatically or with user assistance enhance the image color, brightness or contrast as well as correct for any other distortions.

Software Analysis of the Teeth

The software developed and utilized with the central processor 16 is preferably capable of analyzing the position of each tooth and determining the tooth number (based on standard dental number systems) and may determine the size and surface area of each tooth. To more accurately determine the size and positioning of teeth, the software may first receive data collected from an intra-oral scanner (not shown) and compare the measurements for each tooth as determined by the scanner with those determined by the software.

The central processor 16 is also preferably able to evaluate the progress of aligner cases, including looking at the aligners while on the teeth to confirm fit, etc. The aligners may be evaluated by visual inspection by a human and via software.

A marking or point of orientation can be placed on or identified on one or more of the patient's posterior teeth so that the central processor 16 can determine whether the patient's soft tissue is sufficiently retracted to capture the preferred image of all of the teeth that are expected to be included in the particular image. The marking could be an elastomer or printed marking on the patient's teeth, on hardware or aligners positioned on the patient's teeth or on one of the camera holders 18, 18', 18", 18''', 18'''', 18''''', 18'''''', 18'''''''. Alternatively, the central processor 16 could recognize how many and which teeth are in view and direct the patient that they are collecting acceptable images or there is a deficiency in the image being captured.

User Interface and Lens Selection

The user interface of the central processor 16 preferably facilitates the user selecting the image they wish to capture and automatically selecting the optimal lens and focal point for that particular image. The user interface may have a predetermined image capture sequence or may allow the user to capture images in whatever sequence the user chooses.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

We claim:

1. A camera system for capturing images of a patient's arches and teeth, the camera system comprising:
   a camera having a housing and a lens; and
   a camera holder having an engagement mechanism, an angled column and a positioning block, the engagement mechanism connected to a distal end of the angled column and the positioning block connected to a proximal end of the angled column, the engagement mechanism configured for releasably mounting the camera, the camera lens oriented toward the distal end in a mounted configuration and the positioning block configured to contact the patient's arches, teeth, cheeks or lips when collecting images with the camera, the camera holder orienting the camera lens relative to the patient's arches and teeth, the positioning block or angled column configured for retraction of soft tissue at a single side of the patient's arches.

2. The camera system of claim 1, wherein the camera has a camera axis, the angled column extending at a column axis away from the engagement mechanism, the column axis and the camera axis defining a column angle, the column angle being approximately ten to forty-five degrees.

3. The camera system of claim 1, wherein the engagement mechanism defines an engagement mechanism axis and the camera defines a camera axis, the engagement mechanism axis and the camera axis being coaxial in the mounted configuration.

4. The camera system of claim 1, further comprising:
   a mirror connected to the positioning block, the camera has a camera axis, the camera axis intersecting the mirror.

5. The camera system of claim 1, further comprising:
   a light source connected to the camera holder, the camera has a camera axis, the light source configured to emit light along the camera axis proximate the positioning block and onto the patient's arches and teeth to illuminate the patient's arches and teeth for image capture.

6. The camera system of claim 1, wherein the camera is comprised of a smartphone.

7. The camera system of claim 6, wherein the engagement mechanism has a generally planar portion with a connection slot, a second angled arm including a connection hub that is removably mountable to the connection slot.

8. A method for capturing images of a patient's arches and teeth with a camera defining a camera axis, first hardware, second hardware and a camera holder having a positioning block and an engagement mechanism defining an engagement mechanism axis, the method comprising:
    engaging the camera with the engagement mechanism and the first hardware;
    retracting the patient's lips or cheeks to expose a first desired area of the patient's teeth;
    engaging the positioning block with the patient's teeth, arches, lips or cheeks proximate the first desired area of the patient's teeth, the camera and the camera holder being pivotable relative to the patient's teeth, arches, lips or cheeks about the positioning block;
    orienting the camera axis to intersect the first desired area;
    acquiring a first image of the first desired area with the camera;
    engaging the positioning block with the patient's teeth, arches, lips or cheeks proximate a second desired area of the patient's teeth and the engagement mechanism with the second hardware;
    orienting the camera axis to intersect the second desired area;
    acquiring a second image of the second desired area;
    transmitting the first and second acquired images to a central processor.

9. The method of claim 8, wherein the patient's lips or cheeks are retracted by the camera holder.

10. The method of claim 8, wherein the patient's lips or cheeks are retracted by a tissue retractor.

11. The method of claim 8, wherein the camera is engaged by the engagement mechanism by clamping the camera with the engagement mechanism, the camera axis being coaxial with the engagement mechanism axis when the camera is engaged by the engagement mechanism.

12. The method of claim 8, wherein the first and second desired areas are illuminated by a light source when the first and second images of the first and second desired areas are acquired.

13. The method of claim 8, wherein the first and second acquired images are transmitted to the central processor by wireless or wired transmission protocols.

14. The method of claim 8, wherein the camera is engaged by the engagement mechanism by fastening, adhesive bonding, clamping, snap locking, or bayonet engagement.

15. The method of claim 8, wherein the camera is incorporated into a smartphone, the smartphone connected to the engagement mechanism with an adhesive strip.

16. A method for capturing images of a patient's arches and teeth with a camera defining a camera axis, the method comprising:
    receiving, from a central processor, instructions regarding a desired area of the patient's arches and teeth;
    retracting the patient's lips or cheeks to expose the desired area;
    orienting the camera such that the camera axis intersects the desired area;
    receiving, from the central processor, instructions regarding orienting or spacing the camera relative to the desired area;
    acquiring an image of the desired area with the camera, the desired area is comprised of an occlusal view of a patient's maxillary arch, the central processor determining how much expansion has been achieved through a palatal expander based on comparison of positioning of an expander screw of the palatal expander;
    transmitting the acquired image to the central processor; and
    receiving, from the central processor, instructions regarding acceptance or rejection of the acquired image.

17. The method of claim 16, wherein central processor evaluates progress of an aligner case based on comparing the acquired image of the desired area to previously acquired images of the desired area.

18. The method of claim 16, wherein the processor evaluates a fit of an aligner by comparing positioning of the teeth relative to a shape of the aligner to determine if the fit of the aligner is within an expected fit range of a treatment plan.

19. The method of claim 16, wherein the central processor is comprised of a smartphone and the instructions regarding acceptance or rejection of the acquired image are transmitted from a mobile application of the smartphone.

20. A method for capturing images of a patient's arches and teeth with a camera defining a camera axis, the method comprising:
    receiving, from a central processor, instructions regarding a desired area of the patient's arches and teeth;
    retracting the patient's lips or cheeks to expose the desired area;
    orienting the camera such that the camera axis intersects the desired area;
    receiving, from the central processor, instructions regarding orienting or spacing the camera relative to the desired area;
    acquiring an image of the desired area with the camera, the desired area is comprised of an occlusal view of a patient's maxillary arch, the central processor determining how much expansion has been achieved through a palatal expander based on comparison of the acquired image to a previously acquired image;
    transmitting the acquired image to the central processor; and
    receiving, from the central processor, instructions regarding acceptance or rejection of the acquired image.

* * * * *